US009328051B2

(12) United States Patent
Parker et al.

(10) Patent No.: US 9,328,051 B2
(45) Date of Patent: *May 3, 2016

(54) METHODS AND APPARATUS FOR ISOLATING DICARBOXYLIC ACID

(71) Applicant: Eastman Chemical Company, Kingsport, TN (US)

(72) Inventors: Kenny Randolph Parker, Afton, TN (US); Jennifer Caroline Moffitt, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/141,670

(22) Filed: Dec. 27, 2013

(65) Prior Publication Data

US 2015/0183712 A1     Jul. 2, 2015

(51) Int. Cl.
C07C 51/47 (2006.01)
C07C 51/43 (2006.01)

(52) U.S. Cl.
CPC ............... C07C 51/47 (2013.01); C07C 51/43 (2013.01)

(58) Field of Classification Search
CPC ..................................................... C07C 51/47
See application file for complete search history.

(56) References Cited

U.S. PATENT DOCUMENTS

| 5,200,557 | A | 4/1993 | Gee et al. |
| 5,557,009 | A * | 9/1996 | Izumisawa et al. ........... 562/412 |
| 7,462,736 | B2 | 12/2008 | Parker et al. |
| 7,546,747 | B2 * | 6/2009 | Parker et al. .................... 62/486 |
| 2004/0110981 | A1 | 6/2004 | Sheppard et al. |
| 2004/0245176 | A1 | 12/2004 | Parker et al. |

(Continued)

FOREIGN PATENT DOCUMENTS

EP     1 758 846 B1     6/2009

OTHER PUBLICATIONS

Co-pending U.S. Appl. No. 14/141,639, filed on Dec. 27, 2013.

(Continued)

Primary Examiner — Brian J Davis
(74) Attorney, Agent, or Firm — James Arnold, Jr.

(57) ABSTRACT

Disclosed is a method for purifying aromatic dicarboxylic acid such as isophthalic acid or terephthalic acid. The process treats a crude carboxylic acid (CCA) composition by: a) feeding a CCA composition comprising a liquid and a solid, said liquid comprising an organic solvent and said solids comprising dicarboxylic acid (DCA), to a filter cake formation zone to form: (i) a CCA wet cake composition comprising said DCA solids and a portion of said organic solvent, said CCA wet cake composition having a first liquid level; and (ii) a first mother liquor stream; b) dewatering said CCA wet cake composition to form: (i) a dewatered CCA wet cake composition having a second liquid level that is lower than the first liquid level or having no liquid level; and (ii) a second mother liquor stream; and c) washing the dewatered CCA wet cake composition with a wash stream in a wash zone to form: (i) a washed CCA wet cake composition; and (ii) a wash liquor stream; wherein step b) is performed before step c) by dewatering before a final wash stage is performed, the amount of cobalt metal in the final wet cake product is reduced. The process is flexible in that it allows one to use less wash solvent to obtain an equivalent reduction of cobalt metal in the wet cake composition. Optionally, one may obtain a low moisture wet cake without employing a separate drying step.

75 Claims, 6 Drawing Sheets

(56) References Cited

U.S. PATENT DOCUMENTS

2005/0283022 A1 12/2005 Sheppard
2007/0208198 A1 9/2007 Parker et al.
2007/0208199 A1 9/2007 Parker et al.
2007/0208200 A1 9/2007 Parker et al.

OTHER PUBLICATIONS

USPTO Office Action dated Apr. 9, 2015 in co-pending U.S. Appl. No. 14/141,639.

Notification of Transmittal of the International Search Report and the Written Opinion of the International Searching Authority, or the Declaration date of mailing Jun. 5, 2015 received in International Patent Application No. PCT/US2014/070756.

Notification of Transmittal of the International Search Report and the Written Opinion of the International Searching Authority, or the Declaration date of mailing Jun. 25, 2015 received in International Patent Application No. PCT/US2014/070753.

\* cited by examiner

Prior Art

METHODS AND APPARATUS FOR ISOLATING DICARBOXYLIC ACID

1. FIELD OF THE INVENTION

The present invention relates generally to a product isolation system for use in various carboxylic acid production processes. More specifically, the present invention provides for the efficient removal of catalyst from a crude carboxylic acid slurry while exchanging an organic solvent in the crude carboxylic acid composition with water to produce a water wet cake.

2. BACKGROUND OF THE INVENTION

In conventional terephthalic acid (TPA) or isophthalic acid (IPA) production processes, p-xylene or m-xylene, respectively, undergoes oxidation in the presence of a catalyst and an organic solvent, typically acetic acid, to form a crude terephthalic acid (CTA) or a crude isophthalic acid (CIPA) slurry (collectively referred to herein as a crude carboxylic acid or CCA). The CCA slurry can be further crystallized if desired to improve downstream solid/liquid separation. The TPA or IPA solids in the CCA slurry withdrawn from the primary oxidation reaction vessel or from a crystallization zone are concentrated or isolated in a solid/liquid separation device and washed with a wash organic solvent to remove most of the catalyst, thereby generating a CCA wet cake composition. The CCA wet cake composition is then typically dried to remove any remaining organic solvent such as acetic acid, after which it is slurried in water, and subsequently subjected to catalytic hydrogenation to form a purified terephthalic acid composition (PTA) or a purified isophthalic acid composition (PIPA) (collectively referred to as PCA).

Instead of hydrogenation or in addition to hydrogenation, a slurry of CCA particles withdrawn from the primary oxidation reactor can be subjected to secondary or post oxidation processes to form a PCA composition. It is also desirable to remove as much catalyst as possible for recovery and/or recycling to the primary oxidation zone. Such catalyst recovery can occur prior to entry into or subsequent to the secondary or post oxidation reaction zones.

In a hydrogenation reaction, it is desirable to conduct an organic solvent swap to exchange the organic solvent in the CCA composition for water prior to hydrogenation. In addition, the catalyst contained in the CCA composition is also removed to recover the catalyst and optionally recycle the catalyst to the oxidation zone.

In preparation for hydrogenation, or prior to or after secondary oxidation, the CCA composition is isolated for treatment. Various techniques are available for isolating a CCA composition. An example of one such technique includes the use of batch or continuous vacuum filters, batch or continuous pressure filters, centrifuges and the like. In solid/liquid separation devices, CCA solids are formed into a wet cake and subjected to one or more washes with a wash organic solvent. The purpose of the wash is to minimize the amount of catalyst retained in the CCA wet cake composition 3.

It is desirable to remove as much catalyst as possible from the CCA wet cake composition 3 to have high recovery of catalyst and/or maximize the amount of catalyst that can be recycled to the oxidation zone, as well as reduce the amount of catalyst left in the filter cake which can be detrimental in a hydrogenation reaction or in the process for making reaction products of PCA such as polyesters. In one purification technique, the filter cake is slurried in water and fed to the hydrogenation zone as a slurry. Catalyst retained in the filter cake can carry over into the hydrogenation zone and foul or reduce the activity of the hydrogenation catalyst bed.

In the case that one employs a hydrogenation step, it also becomes necessary to swap the organic solvent in the CCA composition with water. Washing a wet filter cake or a concentrated slurry of CTA and or IPA with water results in the mixing of water with organic solvent that, if the concentration of organic solvent is sufficiently high, would require an organic solvent recovery step before the water can be fed to a waste water treatment facility.

To further ensure that all the organic solvent is removed from the CCA prior to hydrogenation, the wet cake is usually dried before forming a water based slurry of TPA or IPA as a feed to the hydrogenation zone. A drying step, however, requires the input of energy.

It would be desirable to remove as much catalyst as possible in a CCA composition. Alternatively, it would be desirable to exchange the organic solvent with water in a way that reduces the concentration of organic solvent present in the waste water such that a separate organic solvent removal step can be avoided. Alternatively, it would be desirable to provide a process that can avoid, if desired, a drying step before creating a water slurry feed to the hydrogenation reactor. Depending on the purification technique used, it would be ideal if any combination of two or more of these advantages could be realized.

3. SUMMARY OF THE INVENTION

We have discovered a process which efficiently removes a large quantity of catalyst from a CCA slurry and swaps organic solvent with water. There is now provided a process for treating a crude carboxylic acid (CCA) composition comprising: (a) feeding a CCA composition comprising a liquid and solids, said liquid comprising an organic solvent and said solids comprising dicarboxylic acid (DCA), to a filter cake formation zone to form: (i) a CCA wet cake composition comprising said DCA solids and a portion of said organic solvent, said CCA wet cake composition having a first liquid level; and (ii) a first mother liquor stream; (b) dewatering said CCA wet cake composition from step (a) in a dewatering zone to form: (i) a dewatered CCA wet cake composition having a second liquid level that is lower than the first liquid level or having no liquid level; and (ii) a second mother liquor stream; and (c) washing the dewatered CCA wet cake composition from step (b) with a wash stream in a wash zone to form: (i) a washed CCA wet cake composition; and (ii) a wash liquor stream.

By conducting a dewatering step on the filter cake before a cake wash, the amount of catalyst removed is increased and/or the amount of wash required for an equivalent amount of catalyst removal is reduced.

Further, by this technique, it is possible to reduce the amount of organic solvent present in the wash stream, to thereby provide the flexibility of avoiding the use of organic distillation columns prior to feeding the wash stream to waste water treatment. By this technique, a process can now be provided which does not include a step for drying the filter cake before creating a water slurry feed to a hydrogenation zone.

There is also provided a process for treating a crude carboxylic acid (CCA) composition comprising: (a) feeding a CCA composition comprising a liquid and solids, said liquid comprising an organic solvent and said solids comprising dicarboxylic acid (DCA), to a filter cake formation zone to form: (i) a CCA wet cake composition comprising said DCA solids and a portion of said organic solvent, said CCA wet cake composition having a first liquid level; and (ii) a first mother liquor stream; (b) washing said CCA wet cake composition from step (a) with an intermediate wash stream to form: (i) an intermediate washed CCA wet cake composition having a second liquid level that is lower than the first liquid level or having no liquid level; and (ii) an intermediate wash liquor stream; and (c) dewatering said intermediate washed CCA wet cake composition from step (b) to form: (i) a dewatered CCA wet cake composition having a second liquid level that is lower than the first liquid level or having no liquid level; and (ii) a second mother liquor stream; and (d) washing the dewatered CCA wet cake composition from step (c) with a second wash stream in a wash zone to form: (i) a washed CCA wet cake composition; and (ii) a wash liquor stream.

There is further provided a process for treating a crude carboxylic acid (CCA) composition comprising:

A. feeding a CCA composition comprising a liquid and a solid, said liquid comprising an organic solvent and said solids comprising dicarboxylic acid (DCA), to a filter cake formation zone to form:
  (i) a CCA wet cake composition comprising said DCA solids and a portion of said organic solvent, said CCA wet cake composition having a first liquid level; and
  (ii) a first mother liquor stream;
B. washing said CCA wet cake composition with an intermediate wash stream to form:
  (i) an intermediate washed CCA wet cake composition having a second liquid level that is lower than the first liquid level or having no liquid level; and
  (ii) an intermediate wash liquor stream; and
C. dewatering said intermediate washed CCA wet cake composition to form:
  (i) a dewatered CCA wet cake composition having a second liquid level that is lower than the first liquid level or having no liquid level; and
  (ii) a second mother liquor stream; and
D. washing the dewatered CCA wet cake composition with a second wash stream in a wash zone to form:
  (i) a washed CCA wet cake composition comprising no more than 100 ppm of the organic solvent; and
  (ii) a wash liquor stream.

wherein the process does not include a predominantly evaporative drying step.

4. BRIEF DESCRIPTION OF THE DRAWINGS

5. DETAILED DESCRIPTION OF THE INVENTION

Figure 1:
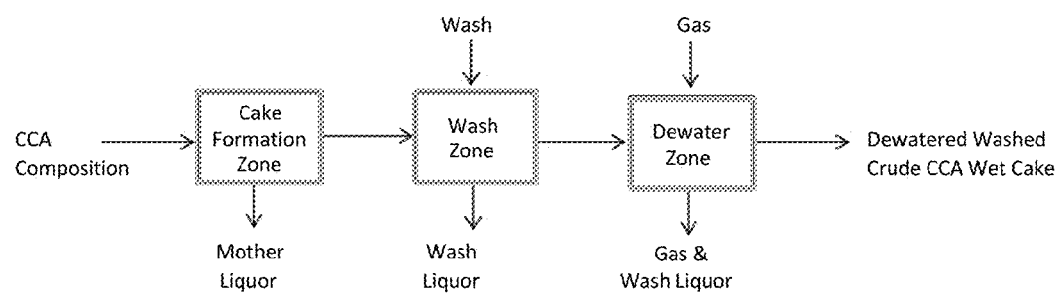
FIG. 1 is a block flow diagram of a comparative process for forming a washed cake followed by making a dewatered crude carboxylic acid cake with a single wash.

An isolation and washing of crude carboxylic acids such as TPA or IPA is illustrated in FIG. 1 as a comparative example to the invention. A CCA slurry is typically routed to a cake formation zone in a solid/liquid separation device to form a wet cake and a mother liquor. The wet cake is then routed to a wash zone where it is contacted with an organic wash solvent to generate a washed CCA wet cake composition and wash liquor composition. The washed CCA wet cake composition is then typically subjected to centrifugal force or a gas stream in a dewatering zone to generate a dewatered washed crude CCA wet cake composition and a mother liquor stream mixed with gas.

Figure 2:
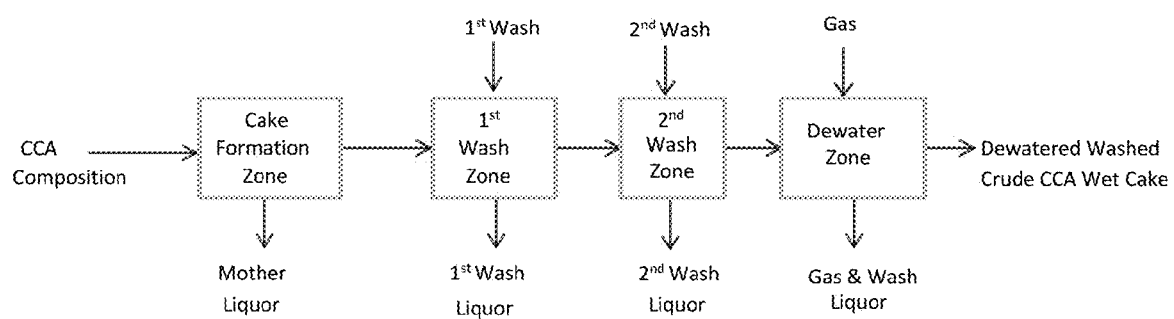
FIG. 2 is a block flow diagram of a comparative process for forming a washed cake followed by making a dewatered crude carboxylic acid cake with a multiple washes preceding a dewatering zone.

FIG. 2 also illustrates a comparative process with multiple washes. A CCA slurry is typically routed to a cake formation zone in a solid/liquid separation device to form a wet cake and a mother liquor. The wet cake is then routed to a wash zone where it is contacted with an organic wash solvent to generate a washed CCA wet cake composition and first wash liquor composition. The washed CCA wet cake composition is then fed to a second wash zone where it is contacted with an organic wash solvent to generate a washed CCA wet case and a second wash liquor composition stream. In this configuration, the wash streams are typically countercurrent washes in which the wash liquor from the second wash zone is used as the feed to the first wash zone. The washed CCA wet cake composition is then typically subjected to centrifugal force or a gas stream in a dewatering zone to generate a dewatered washed crude CCA wet cake composition and a mother liquor stream mixed with gas.

There is now provided a process for treating a crude carboxylic acid (CCA) composition comprising:

A. feeding a CCA composition comprising a liquid and a solid, said liquid comprising an organic solvent and said solids comprising dicarboxylic acid (DCA), to a filter cake formation zone to form:
  (i) a CCA wet cake composition comprising said DCA solids and a portion of said organic solvent, said CCA wet cake composition having a first liquid level; and
  (ii) a first mother liquor stream;
B. dewatering said CCA wet cake composition to form:
  (i) a dewatered CCA wet cake composition having a second liquid level that is lower than the first liquid level or having no liquid level; and
  (ii) a second mother liquor stream; and
C. washing the dewatered CCA wet cake composition with a wash stream in a wash zone to form:
  (i) a washed CCA wet cake composition; and
  (ii) a wash liquor stream;

wherein step B is performed before step C.

There is also provided a process for treating a crude carboxylic acid (CCA) composition comprising:

A. feeding a CCA composition comprising a liquid and a solid, said liquid comprising an organic solvent and said solids comprising dicarboxylic acid (DCA), to a filter cake formation zone to form:
 (i) a CCA wet cake composition comprising said DCA solids and a portion of said organic solvent, said CCA wet cake composition having a first liquid level; and
 (ii) a first mother liquor stream;
B. dewatering said CCA wet cake composition in a dewatering zone to form:
 (i) a dewatered CCA wet cake composition having a second liquid level that is lower than the first liquid level or having no liquid level; and
 (ii) a second mother liquor stream; and
C. washing the dewatered CCA wet cake composition with a wash stream in a wash zone to form:
 (i) a washed CCA wet cake composition comprising no more than 100 ppm of the organic solvent; and
 (ii) a wash liquor stream;
wherein the process does not include a predominantly evaporative drying step.

Reference is made to FIGS. 3-6 to further describe the invention. In step A, a CCA composition is fed to a filter cake formation zone. Further, references to treating a composition obtained from a prior step can include a direct or indirect feed of that composition from the prior step. An indirect feed means that the composition from the prior step can have been treated with any intervening process, including but not limited to other wash and/or dewatering steps, before it reached the step under consideration. For example, a description of, "dewatering said CCA wet cake composition to form . . . " is not limited to the CCA wet cake composition obtained directly from the filter cake formation zone, and can include any number of intervening steps between the filter cake formation zone to the dewatering zone, unless it is expressly stated that the feed to the dewatering zone is a direct feed of CCA wet cake composition obtained from the filter cake formation zone. A description of, "dewatering said CCA wet cake composition to form . . . " is a reference to indicate that the feed to the dewatering zone has to at least have gone through a preceding filter cake formation zone to form a CCA wet cake composition, leaving open the possibility that the composition can change before it is ultimately fed to the dewatering zone. Such additional intervening steps are illustrated in other some of the figures, e.g. FIG. 5.

References to ranges and numbers within a range include the end points of the ranges.

The CCA composition is a composition containing solids and a liquid organic solvent. The CCA composition is desirably a slurry. The CCA composition fed to the filter cake formation zone desirably has not been subjected to a step designed to hydrogenate the carboxylic acid.

At least a portion of the solids in the CCA composition are aliphatic, aromatic, or alicyclic containing dicarboxylic acid ("DCA") solids. Desirably, the DCA solids in the CCA composition comprise aromatic containing dicarboxylic acids compounds. For example, the solid particles in the CCA composition can comprise mono-nuclear aromatic dicarboxylic acid molecules. Desirably, the solid particles in the CCA composition comprise TPA or IPA molecules or a mixture thereof.

The solid particles can have an average concentration of DCA in the solids of at least 50 weight percent, or at least 65 weight percent, or at least 75 weight percent, or at least 80 weight percent, or at least 85 weight percent, or at least 90 weight percent, or at least 93 weight percent, or at least 95 weight percent, or at least 97 weight percent, or at least 98 weight percent, and in each case less than 100%, based on the weight of the solids. Other materials, compounds, or oligomers in the solids include catalyst metals, by-products formed during oxidation of the feedstock into a primary oxidation zone to make the CCA composition, and impurities in the feedstock to the primary oxidation zone that carry over into the CCA composition or which are reacted to produce by-products that carry over into the CCA composition.

The amount of DCA solids in the CCA composition is not particularly limited and can be at least 10 wt. %, or at least 15 wt. %, or at least 20 wt. %, or at least 25 wt. %, or at least 28 wt. %, or at least 30 wt. %, or at least 32 wt. %, or at least 34 wt. %, or at least 35 wt. %, or at least 37 wt. %, or at least 38 wt. %, or at least 39 wt. %, or at least 40 wt. %, or at least 42 wt. %. Generally, the process produces up to 60 wt. %, or up to 55 wt. %, or up to 50 wt. % solids. Suitable ranges include solids in an amount ranging from 10 to 45 weight percent, or 15 to 45 weight percent, or from 20 to 45 weight percent, or from 25 to 45 weight percent, or from 10 to 40 weight percent, or from 15 to 40 weight percent, or from 20 to 40 weight percent, or from 25 to 40 weight percent, or from 10 to 38 wt. %, or from 15 to 38 wt. %, or from 20 to 38 wt. %, or from 25 to 38 wt. %, or from 10 to 35 wt. %, or from 15 to 35 wt. %, or from 20 to 35 wt. %, or from 25 to 35 wt. %, in each case based on the weight of the CCA composition.

The DCA solids in the CCA composition can have a mean particle size of at least 10 microns. Suitable mean particle sizes range from 10 to 500 microns, or 20 to 400 microns, or 30 to 300 microns, as a mean particle size.

The CCA composition also comprises a liquid phase. The liquid phase is desirably the remainder of any one of the above mentioned quantities of solids in the CCA composition less entrained gas, if any. The liquid phase can be present in an amount ranging from 50 and up to 99 weight percent. For example, the liquid phase can be present in an amount ranging from 95 to 65 weight percent, or in the range of from 85 to 55 weight percent, or from 80 to 55 weight percent, or from 75 to 55 weight percent, or from 95 to 60 weight percent, or from 85 to 60 weight percent, or from 80 to 60 weight percent, or from 75 to 60 weight percent, or from 95 to 62 wt. %, or from 85 to 62 wt. %, or from 80 to 62 wt. %, or from 75 to 62 wt. %, or from 95 to 65 wt. %, or from 85 to 65 wt. %, or from 80 to 65 wt. %, or from 75 to 65 wt. %, in each case based on the weight of the CCA composition.

The liquid of the CCA composition comprises an organic solvent. The organic solvent desirably comprises an organic acid, such as an organic low molecular weight monocarboxylic acid having from 1 to 6 carbon atoms, or 1 to 2 carbon atoms. For example, the organic solvent comprises acetic acid. The acid component can make up at least 75 weight percent of the liquid phase, or at least 80 weight percent of the liquid phase, and in each case up to 100% of the liquid phase. An example of a range of acid component in the organic solvent is an acid component in the range of from 85 to 98 weight percent of the liquid phase, with the balance being water.

The CCA composition can contain, in addition to DCA solids, water, and organic solvent, ingredients such as metals, by-products and impurities (collectively "impurities" for convenience) in both the liquid phase and in or on the solids. Such impurities can include oxidation byproducts formed during the at least partial oxidation of the above-mentioned oxidizable compound, including, but not limited to, benzoic acid (BA), bromo-benzoic acid, bromo-acetic acid, isophthalic acid in the liquid phase, terephthalic acid in the liquid phase, trimellitic acid, 2,5,4"-tricarboxybiphenyl, 2,5,4"-tricarboxybenzophenone, para-toluic acid (p-TAc), 4-carboxybenzaldehyde (4-CBA), monocarboxyfluorenones, and/or dicarboxyfluorenones.

For example, the CCA composition can contain IPA solids, organic solvent, water, and the following impurities, in each case based on the weight of the CCA composition:
benzoic acid in an amount ranging from 300 to 800 ppmw;
meta-toluic acid in an amount ranging from 200 to 700 ppmw;
3-carboxybenxaldehyde in an amount ranging from 800 to 1250 ppmw.

The CCA composition can contain, in addition to TPA solids, organic solvent, and water, the following impurities based on the weight of the CCA composition:
benzoic acid in an amount ranging from 300 to 800 ppmw;
para-toluic acid in an amount ranging from 150 to 350 ppmw;
4-carboxybenzaldehyde in an amount ranging from 2000 to 3000 ppmw.

The level of at least one of these impurities, or a lease two of these impurities, or each of these impurities in the washed CCA wet cake composition can be reduced by more than 50 wt. %, or more than 60 wt. %, or more than 70 wt. % using the process of the invention.

The CCA composition fed to the filter cake formation zone is a crude composition, meaning that the composition undergoing treatment and fed to the filter cake formation zone is crude carboxylic acid composition containing solids and liquids that has been withdrawn from a primary oxidation zone, a secondary oxidation zone, or a post oxidation zone, but that has not been subjected to a step for hydrogenation, and optionally but desirably has also not been subjected to a step of solid/liquid separation. The CCA composition may undergo additional process steps after it is removed from the primary oxidation zone and before entry into the filter cake formation zone. An example of such a process step secondary or post oxidation, and/or crystallization to increase the concentration of solids in the CCA composition.

An example of such an oxidation process for making the CCA composition can comprise introducing a predominately fluid-phase feed stream containing an oxidizable compound (e.g., para-xylene for TPA or m-xylene for IPA), an organic solvent (e.g., acetic acid and/or water), and a catalyst system (e.g., cobalt, manganese, and/or bromine) into an oxidation reactor (not shown). A predominately gas-phase oxidant stream containing molecular oxygen can also be introduced into the oxidation reactor. The fluid- and gas-phase feed streams can form a multi-phase reaction medium in the oxidation reactor. The oxidizable compound can undergo at least partial oxidation in a liquid phase of the reaction medium contained in the oxidation reactor.

Suitable examples of the oxidizable compound include, but are not limited to, para-xylene, meta-xylene, para-toluadehyde, meta-tolualdehyde, para-toluic acid, and/or meta-toluic acid. In one embodiment of the present invention, the oxidizable compound comprises para-xylene.

The organic solvent present in the fluid-phase feed stream introduced into the oxidation reactor can comprise an acid component and a water component. The organic solvent can be present in the fluid-phase feed stream in amounts as mentioned above.

The fluid-phase feed stream introduced into the oxidation reactor can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from 300 to 6,000 parts per million by weight (ppmw), in the range of from 700 to 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from 300 to 5,000 ppmw, in the range of from 600 to 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from 20 to 1,000 ppmw, in the range of from 40 to 500 ppmw, or in the range of from 50 to 200 ppmw. Optionally the catalyst may also comprise zinc. Each of these metals may be in any oxidation state, including zero, +1, or +2 oxidation state, and may be charged as inorganic or organic salts, such as carboxylates.

The quantity of all catalyst metals in the CCA composition can range from at least 2500, or at least 3000, or at least 3500, or at least 4000, and up to 10,000, or up to 7000, or up to 6000, or up to 5500, in each case based on the weight of the CCA composition. Suitable ranges include any combination of the above. As example, a cumulative quantity of catalyst metals in the CCA composition can range from 2500 ppm to 10,000 ppm, or 3000 to 10,000 ppm, or 3500 to 10,000 ppm, or 4000 to 10,000 ppm, or 2500 ppm to 7,000 ppm, or 3000 to 7,000 ppm, or 3500 to 7,000 ppm, or 4000 to 7,000 ppm, 2500 ppm to 6,000 ppm, or 3000 to 6,000 ppm, or 3500 to 6,000 ppm, or 4000 to 6,000 ppm, 2500 ppm to 5,500 ppm, or 3000 to 5,500 ppm, or 3500 to 5,500 ppm, or 4000 to 5,500 ppm, in each case based on the weight of the CCA composition.

In one embodiment of the present invention, cobalt and bromine can both be present in the catalyst system. The weight ratio of cobalt to bromine (Co:Br) in the catalyst system can be in the range of from 0.25:1 to 4:1, in the range of from 0.5:1 to 3:1, or in the range of from 0.75:1 to 2:1. In another embodiment, cobalt and manganese can both be present in the catalyst system. The weight ratio of cobalt to manganese (Co:Mn) in the catalyst system can be in the range of from 0.3:1 to 40:1, in the range of from 5:1 to 30:1, or in the range of from 10:1 to 25:1.

During oxidation, the oxidizable compound (e.g., para-xylene or m-xylene) can be continuously introduced into the oxidation reactor at a rate of at least 5,000 kilograms per hour, at a rate in the range of from 10,000 to 80,000 kilograms per hour, or in the range of from 20,000 to 50,000 kilograms per hour. During oxidation, the ratio of the mass flow rate of the organic solvent to the mass flow rate of the oxidizable compound entering the oxidation reactor can be maintained in the range of from 2:1 to 50:1, in the range of from 5:1 to 40:1, or in the range of from 7.5:1 to 25:1.

The predominately gas-phase oxidant stream introduced into the oxidation reactor can comprise in the range of from 5 to 40 mole percent molecular oxygen, in the range of from 15 to 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises 21 mole percent molecular oxygen and 78 to 81 mole percent nitrogen. In an alternative embodiment of the present invention, the oxidant stream can comprise substantially pure oxygen.

During liquid-phase oxidation in the oxidation reactor, the oxidant stream can be introduced into the oxidation reactor in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering the oxidation reactor can be maintained in the range of from 0.5:1 to 20:1, in the range of from 1:1 to 10:1, or in the range of from 2:1 to 6:1.

The liquid-phase oxidation reaction carried out in the oxidation reactor can be a precipitating reaction that generates solids. In one embodiment, the liquid-phase oxidation carried out in the oxidation reactor can cause at least 10, or at least 40, or at least 70, or at least 80, or at least 90 weight percent of the oxidizable compound introduced into the oxidation reactor to form CA solids in the reaction medium. The solids content in the reaction medium are as mentioned above with respect to the solids content in the CCA composition.

During oxidation in the oxidation reactor, the multi-phase reaction medium can be maintained at an elevated temperature in the range of from 125 to 200° C., in the range of from 150 to 180° C., or in the range of from 155 to 165° C. The overhead pressure in the oxidation reactor can be maintained in the range of from 1 to 20 bar gauge (barg), in the range of from 2 to 12 barg, or in the range of from 4 to 8 barg.

A CCA slurry can be withdrawn from an outlet of the oxidation reactor. The solid phase of the crude slurry can be formed primarily of DCA with some impurities. The liquid phase of the crude slurry can be a mother liquor comprising at least a portion of the organic solvent, one or more catalyst components, and minor amounts of dissolved DCA, as well as the impurities.

Subsequent to removal from the oxidation reactor, at least a portion of the CCA composition can be purified in a purification zone if desired. The CCA composition can be treated to reduce the concentration of at least one of the above-mentioned impurities. Such reduction in the concentration of impurities in the CCA composition can be accomplished by oxidative digestion, hydrogenation, and/or dissolution/recrystallization. The process of the invention can be used to treat a CCA composition withdrawn from a primary oxidation reactor and prior to oxidative digestion (secondary oxidation), or prior to a step for recrystallization, or prior to a step for hydrogenation, or prior to any step for the further purification of the CCA composition. Alternatively, the process of the invention can be used to treat a CCA composition after it is withdrawn from an oxidative digestion step, and before hydrogenation or downstream recrystallization. Desirably, in all cases the process of the invention is used to treat a CCA composition prior to hydrogenation.

The temperature of the CCA feed to the filter cake formation zone is not limited. Generally, the temperature of the CCA composition feed is at least 40° C., in the range of from 40 to 195° C., in the range of from 50 to 160° C., or in the range of from 60 to 140° C., as measured immediately upon being introduced into filter cake formation zone 1 as shown in FIG. 3.

The process of the invention is desirably a continuous process.

Figure 3:
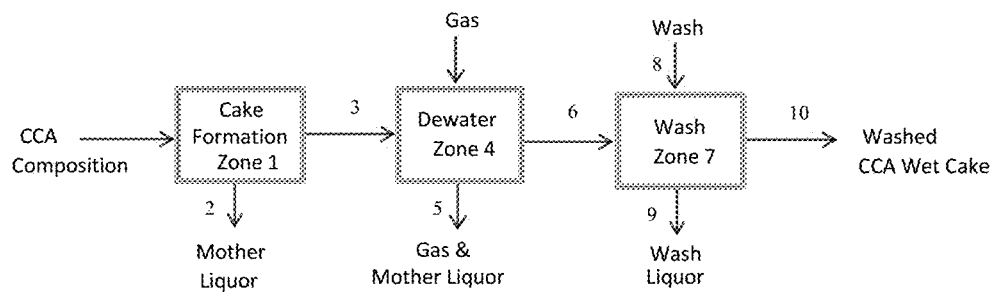
FIG. 3 is a block flow diagram of a process of the invention for forming a dewatered and washed crude carboxylic acid cake with a single wash in which dewatering occurs prior to a washing step.

As shown in FIG. 3, the CCA composition, typically in the form of a slurry, is fed to a filter cake formation zone 1 to form a first mother liquor composition in stream 2 and a CCA wet cake composition 3 comprising DCA solids and a portion of the organic solvent. The CCA wet cake has a first level of liquid. The CCA wet cake composition contains a higher concentration of DCA solids based on the CCA wet cake composition relative to the concentration of DCA in the CCA composition fed to the filter cake formation zone 1. A portion of the organic solvent is removed from the CCA composition and discharged as a mother liquor stream 2. Desirably, the concentration of organic solvent in the CCA wet cake composition is lower than the concentration of organic solvent in the CCA composition fed to the filter cake formation zone.

The mother liquor composition discharged from the filter cake formation zone 1 as mother liquor stream 2 can comprise organic solvent, water, one or more catalyst components, oxidation byproducts, and dissolved DCA. The mother liquor can comprise organic solvent in an amount of at least 85 weight percent, at least 95 weight percent, or at least 99 weight percent, based on the weight of the mother liquor stream.

The catalyst components in the mother liquor stream 2 can comprise the catalyst components as described above with reference to the catalyst system introduced into the oxidation reactor (e.g., cobalt, manganese, and/or bromine). The mother liquor can have a cumulative concentration of all of the catalyst components in the range of from 500 to 20,000 ppmw, in the range of from 1,000 to 15,000 ppmw, or in the range of from 1,500 to 10,000 ppmw, based on the weight of the mother liquor stream.

The oxidation byproducts in the mother liquor can comprise one or more of the oxidation byproducts discussed above. In one embodiment, the mother liquor can have a cumulative concentration of all of the oxidation byproducts in the range of from 1,000 to 200,000 ppmw, in the range of from 2,000 to 120,000 ppmw, or in the range of from 3,000 to 60,000 ppmw, based on the weight of the mother liquor stream.

The mother liquor stream 2 discharged from the filter cake formation zone 1 can optionally contain solids, desirably in an amount of less than 5 weight percent, less than 2 weight percent, or less than 1 weight percent. Additionally, the mother liquor composition stream 2 can have a temperature of less than 240° C., in the range of from 20 to 200° C., or in the range of from 50 to 100° C.

The CCA wet cake composition formed in the filter cake formation zone 1 has a first liquid level as determined by the CCA wet cake composition at the exit of filter cake formation zone. The filter cake has a bottom surface and a top surface. The bottom surface of the CCA wet cake composition, and for that matter, any of the other wet cake compositions in subsequent zones, is the surface of the wet cake contacting the filter media. The top surface of any wet cake is the highest continuous surface disposed opposite from the bottom surface. The liquid level in the CCA wet cake composition can be at or above the top surface.

The height of the filter cake is the average distance between the top and bottom surface of the CCA wet cake. A liquid level can be at the top surface of the CCA wet cake, meaning that the liquid is at the top surface of any valley in the wet cake to the extent that the wet cake does not have a uniform top surface, and desirably, the liquid level is at the top surface of any crest on the CCA wet cake top surface. It is desirable that the first liquid level is above the top surface of the CCA wet cake, meaning that the top surface is submerged under the liquid level. For example, the first liquid level can be at the top surface of the CCA wet cake, or it can be above the CCA wet cake top surface at a distance of no more than 0.1 inches above the top surface, or no more than 0.2 inches, or no more than 0.3 inches, or no more than 0.4 inches, or no more than 0.5 inches, or no more than 0.8 inches, or no more than 1 inch, or no more than 1.5 inches, or no more than 2 inches, or no more than 2.5 inches, or no more than 3 inches, or no more than 3.5 inches, or no more than 4 inches, or no more than 4.5 inches, or no more than 5 inches, in each case above the top surface of the CCA wet cake. Desirably, the first liquid level can be within a range from 0/5 (meaning at the top surface to 5 inches above the top surface), or within a range of 4/5 (meaning within a range of 4 inches to 5 inches above the top surface), or 3.5/5, or 3/5, or 2.5/5, or 2/5, or 1.5/5, or 1/5, or 0.5/5, or 0.2/5, or 0.1/5, or 4/4, or 3.5/4, or 3/4, or 2.5/4, or 2/4, or 1.5/4, or 1/4, or 0.5/4, or 0.2/4, or 0.1/4, or 0/4, or 2.5/3, or 2/3, or 1.5/3, or 1/3, or 0.5/3, or 0.2/3, or 0.1/3, or 0/3, or 1.5/2, or 1/2, or 0.5/2, or 0.2/2, or 0.1/2, or 0/2, or 0.5/1, or 0.2/1, or 0.1/1, or 0/1, or 0.5/0.8, or 0.2/0.8, or 0.1/0.8, or 0/0.8, or 0.2/0.4, or 0.1/0.4, or 0/0.4, or 0.1/0.2, or 0/0.2, or 0/0.1.

The liquid level heights described above are also applicable to the liquid levels at or above the wet cakes in any one or more of the wash zones described further below.

The composition of the first liquid level in the CCA wet cake composition comprises the organic solvent present in the CCA composition fed to the CCA filter cake formation zone. Desirably, at least 50 wt. %, or at least 60 wt. %, or at least 70 wt. %, or at least 80 wt. %, or at least 90 wt. %, or at least 95 wt. %, or at least 98 wt. %, or at least 99 wt. %, or 100 wt % of the first liquid level comprises the same liquid composition as the liquid present in the CCA composition. Desirably, the first liquid level contains an organic solvent, and at least 50 wt. %, or at least 60 wt. %, or at least 70 wt. %, or at least 80 wt. %, or at least 90 wt. %, or at least 95 wt. %, or at least 98 wt. %, or at least 99 wt. %, or 100 wt % of the organic solvent in the first liquid level is the same organic solvent in the CCA composition fed to the filter cake formation zone.

The pressure within the filter cake formation zone 1 is not limited. Suitable pressures range from 1 to 5 bar gauge, 2 bar to 5 bar gauge, 3 bar to 4 bar gauge. In vacuum filtration, the pressure within the filter cake formation zone 1 can range from 0.3 bar absolute to less than 1 bar absolute The temperature within the filter cake formation zone 1 is not limited. Suitable temperatures range from 70° C. to 140° C. The residence time of the CCA composition in the filter cake formation zone 1 can range from 2 seconds to 60 seconds, from 3 seconds to 30 seconds, from 5 seconds to 20 seconds, and from 6 seconds to 17 seconds. The CCA wet cake composition thickness can be from 0.5 inches to 5 inches, or 1 inch to 5 inches, or 2 inches to 5 inches, or 3 inches to 5 inches, or 4 inches to 5 inches.

The CCA wet cake composition 3 comprising DCA solids and organic solvent is fed to a dewatering zone 4 as shown in FIG. 3. In the dewatering zone 4, the weight % of the liquid phase is reduced, and the liquid phase can be water, liquids other than water, or combinations thereof. As used throughout the specification, a dewatering zone is a term of art that is not limited to the displacement of water, and can include the displacement of other liquids instead of or as well as water. The CCA wet cake composition is dewatered to form a second mother liquor stream 5 and a dewatered wet cake composition 6. The dewatered cake composition has a second liquid level or no liquid level. In a no liquid level, the dewatered cake is substantially free of liquid. Surfaces of solids will be wet, but not contain a liquid level in the dewatered cake). The concentration of DCA solids in the dewatered wet cake composition 6 is desirably higher than the concentration of DCA solids in the CCA wet cake composition 3.

In the process of dewatering, the CCA wet cake composition 3 fed to the dewater zone 4 is contacted with a force to physically displace at least a portion of the liquid present in the CCA wet cake composition within the dewatering zone, such as by contacting the CCA wet cake composition in the dewatering zone with a stream, said stream comprising a gas, as shown in FIG. 3, or by exerting a vacuum on the CCA wet cake composition. The force acting on the CCA wet cake composition displaces at least a portion of the mobile phase of the CCA wet cake composition (e.g. the liquid phase), leaving a solids portion on the filter media having a reduced content of the mobile phase (meaning a continuous mobile phase) or no mobile phase remaining, in which case the dewatered wet cake solids are wetted on their surface only, although isolated pockets of discontinuous liquid phase can be present. The gas stream contacting the CCA wet cake composition can be motive or flowing when contacting the wet cake. The gas stream comprises an inert gas or air. The gas can be dried and/or dehumidified prior to its introduction into the dewatering zone. In one embodiment, the stream feeding the dewatering zone can comprise a gas, and such stream can comprise at least 80 volume % gas, or at least 85 volume % gas, or at least 90 volume % gas, or at least 95 volume % gas, or at least 98 volume % gas, or at least 99 volume % gas, or at least 99.5 volume % gas, or at least 99.7 volume % gas, or at least 99.8 volume % gas, or at least 99.9 volume % gas, or at least 99.95 volume % gas, or at least 99.98 volume % gas, or at least 99.99 volume % gas, and in each case, the gas can comprise at least 90 wt. % air, nitrogen, or inert gases other than nitrogen, and desirably nitrogen. The flow rate per unit area of the gas stream fed to the dewatering zone can be 0.04-0.14 L/min/cm$^2$. The CCA wet cake composition in the dewatering zone is desirably under positive pressure. Suitable temperatures range from 60° C. to 140° C.

The direction at which the gas is set to flow is not limited. Gas can flow substantially perpendicular to the filter media retaining the wet cake.

The second mother liquor stream 5 is discharged from the dewatering zone 4. The second mother liquor stream 5 discharged from the dewatering zone can comprise organic solvent, water, one or more catalyst components, oxidation byproducts, and dissolved DCA. The second mother liquor can comprise organic solvent in an amount of at least 85 weight percent, at least 95 weight percent, or at least 99 weight percent, based on the weight of the second mother liquor stream 5.

The catalyst components in the second mother liquor can comprise the catalyst components as described above with reference to the catalyst system introduced into the oxidation reactor (e.g., cobalt, manganese, and/or bromine). The second mother liquor can have a cumulative concentration of all of the catalyst components in the range of from 500 to 20,000 ppmw, in the range of from 1,000 to 15,000 ppmw, or in the range of from 1,500 to 10,000 ppmw, based on the weight of the second mother liquor stream 5.

The oxidation byproducts in the second mother liquor can comprise one or more of the oxidation byproducts discussed above. In one embodiment, the second mother liquor can have a cumulative concentration of all of the oxidation byproducts in the range of from 1,000 to 200,000 ppmw, in the range of from 2,000 to 120,000 ppmw, or in the range of from 3,000 to 60,000 ppmw, based on the weight of the mother liquor stream.

The second mother liquor stream 5 can contain a portion of the gas fed to the dewatering zone. The second mother liquor stream 5 can comprise a liquid/gas phase, wherein at least a portion of the gas fed to the dewatering zone 4 is in the second mother liquor stream, or the entire gas stream fed to the dewatering zone 4 is in the second mother liquor stream. The amount of gas contained in the second mother liquor stream 5 can be less than 10%, less than 5%, less than 3%, less than 1%, less than 0.5%, each on a mass basis, and greater than 0, or at least 0.05%, or at least 0.1% on a mass basis, based on the weight of the second mother liquor stream 5.

The second mother liquor composition in stream 5 discharged from the dewatering zone 4 can comprise solids in an amount of less than 2 weight percent, or less than 1 weight percent. Additionally, the second mother liquor composition 5 can have a temperature of less than 240° C., and be in the range of from 20 to 200° C., or in the range of from 50 to 100° C.

The second mother liquor stream can, if desired, have the substantially the same composition as the first mother liquor stream. By substantially is meant that the concentration of the two ingredients having the highest concentration by weight percent in the first mother liquor stream at within +/−5 units of the same ingredients in the second mother liquor stream. If desired, the identity can be even closer, to +/−4 units, or +/−3 units, or +/−2 units, or +/−1 unit. Further if desired, the identity can be between 3, or 4, or 5 ingredients having the highest concentration by weight percent in the first mother liquor stream and the same ingredients in the second mother liquor stream.

The second mother liquor stream quantity can be greater than or less than the quantity of the first mother liquor stream. Desirably, the second mother liquor stream quantity is less than the quantity of the first mother liquor stream. The weight ratio of first mother liquor stream to the second mother liquor stream can be at least 0.5:1, or at least 1:1, but is desirably at least 1.5:1, or at least 2:1, or at least 3:1, or at least 4:1, or at least 5:1, or at least 6:1, or at least 7:1, or at least 8:1, or at least 9:1, or at least 10:1.

The liquid volume of the second mother liquor stream 5 is less than the liquid volume of the first mother liquor stream 2. Desirably, the ratio of the liquid volume of the second mother liquor stream 5 to the liquid first mother liquor stream 2 is less than 0.9:1, or less than 0.8:1, or less than 0.7:1, or less than 0.6:1, or less than 0.5:1, or less than 0.4:1, or less than 0.3:1, or less than 0.2:1, or less than 0.1:1, or less than 0.05:1, or less than 0.02:1, or less than 0.01:1, or less than 0.005:1.

The pressure within the dewatering zone is not limited. Suitable pressures range from 1 to 5 bar gauge, 2 bar to 5 bar gauge, 3 bar to 4 bar gauge. In vacuum filtration, the pressure within the dewatering zone can range from 0.3 bar absolute to less than 1 bar absolute. The temperature within the dewatering zone is not limited. Suitable temperatures range from 70° C. to 140° C. The residence time CCA wet cake composition in the dewatering zone can range from 2 seconds to 60 seconds, from 3 seconds to 30 seconds, from 5 seconds to 20 seconds, and from 6 seconds to 17 seconds. The dewatered wet cake thickness can be from 0.5 inches to 5 inches, or 1 inch to 5 inches, or 2 inches to 5 inches, or 3 inches to 5 inches, or 4 inches to 5 inches.

The dewatered wet cake composition as used herein means a wet cake composition that have has a second liquid level lower than the first liquid level or no continuous liquid level. The dewatered wet cake has a top and bottom surface and a height. The bottom surface of the dewatered wet cake composition is the lowest surface of the wet cake in the filter cake formation zone. The top surface is the highest continuous surface disposed opposite from the bottom surface. The height is the distance from the bottom surface to the top surface and is an average height across the dewatered cake.

The second liquid level is lower than the first liquid level. Desirably, the second liquid level is at least below the top surface of the dewatered cake composition. The second liquid level has a height that is no more than 90%, or no more than 80%, or no more than 70%, or no more than 60%, or no more than 50%, or no more than 40%, or no more than 30%, or no more than 20%, or no more than 15%, or no more than 10%, or no more than 8%, or no more than 5%, or no more than 4%, or no more than 3%, or no more than 2%, or no more than 1%, of the average height of the dewatered wet cake. Alternatively, the second liquid level can be within 4 inches, or within 3.5 inches, or within 3 inches, or within 2.5 inches, or within 2 inches, or within 1.5 inches, or within 1 inch, or within 0.5 inches, or within 0.4 inches, or within 0.3 inches, or within 0.2 inches, or within 0.1 inches above the bottom surface of the dewatered wet cake. The ratio between the height of the second liquid level to the height of the first liquid level can be any amount below 1:1, such as less than 0.95:1, or less than 0.90:1, or less than 0.85:1, or less than 0.80:1, or less than 0.75:1, or less than 0.70:1, or less than 0.65:1, or less than 0.60:1, or less than 0.55:1, or less than 0.50:1, or less than 0.45:1, or less than 0.40:1, or less than 0.35:1, or less than 0.30:1, or less than 0.25:1, or less than 0.20:1, or less than 0.15:1, or less than 0.10:1, or less than 0.05:1, or less than 0.04:1, or less than 0.03:1, or less than 0.02:1, or less than 0.01:1, or less than 0.008:1, or less than 0.007:1, or less than 0.005:1, or less than 0.003:1, or less than 0.002:1, or less than 0.001:1.

The dewatered wet cake composition may have no liquid level. A liquid level is a mobile continuous phase of liquid. The dewatering may be so efficient in the dewatering zone that the dewatered cake composition does not have a liquid level, meaning that the cake does not have a mobile continuous phase of liquid across the bottom surface of the cake. While the moisture on the cake particles can be in contact and all the particles can contact each other to form a continuous string of contact between moist particles, it does not constitute a liquid level if the moisture is insufficient for form a liquid that is both a continuous phase and is mobile. A dewatered wet cake composition can have moisture without having a liquid level. The percentage moisture on the dewatered wet cake that has no liquid level can be, by weight percent of the dewatered wet cake composition, can be 90 wt. % or less, or 85 wt. % or less, or 80 wt. % or less, or 75 wt. % or less, or 70 wt. % or less, or 65 wt. % or less, or 60 wt. % or less, or 55 wt. % or less, or 50 wt. % or less, or 45 wt. % or less, or 40 wt. % or less, or 35 wt. % or less, or 30 wt. % or less, or 25 wt. % or less, or 20 wt. % or less, or 15 wt. % or less, or 14 wt. % or less, or 13 wt. % or less, or 12 wt. % or less, or 11 wt. % or less, or 10 wt. % or less, or 9 wt. % or less, or 8 wt. % or less, or 7 wt. % or less, or 6 wt. % or less, or 5 wt. % or less, and in each case at least 1 wt. % or more.

The dewatered wet cake composition 6 is fed to a wash zone 7 as shown in FIG. 3 and washed with a wash stream 8 to generate a wash liquor composition as stream 9 and a washed CCA wet cake composition 10. In the wash zone 7, the dewatered wet cake composition 6 is contacted with a wash stream 8 fed to the wash zone 7 that contacts the dewatered wet cake composition. The wash stream 8 can be water, an organic solvent, or a mixture thereof. The organic wash solvent composition will depend upon the desired composition of the washed CCA wet cake composition. For example, if the washed CCA wet cake composition will be fed directly or indirectly to a hydrogenation step in which the presence of acetic acid is not desired, the wash stream 8 will comprise water, desirably in an amount of greater than 30 wt. %, or at least 40 wt. %, or at least 50 wt. %, or at least 60 wt. %, or at least 70 wt. %, or at least 80 wt. %, or at least 90 wt. %, or at least 95 wt. %, or at least 98 wt. %, or at least 99 wt. %, based on the weight of the wash stream 8 composition. Alternatively, the washed CCA wet cake composition can be an acid wet cake if desired, in which case the wash solvent desirably comprises an organic solvent such as acetic acid or a mixture of water and acetic acid. Desirably, the concentration of organic solvent in the wash stream 8, such as acetic acid, is at least 50 wt. %, or at least 60 wt. %, or at least 70 wt. %, or at least 80 wt. %, or at least 90 wt. %, or at least 95 wt. %, or at least 98 wt. %, or at least 99 wt. %, based on the weight of the feed of wash stream 8.

The amount of wash water or organic solvent fed to the wash zone 7 is not limited. The amount of wash stream fed to the wash zone 7 is desirably at a wash ratio (defined as the mass of wash/mass of dry solids in the dewatered wet cake composition 6) from at least 0.2:1, or at least 0.3:1, or at least 0.4:1, or at least 0.5:1, or at least 0.6:1. There is no particular upper limit, but for economy, a wash ratio of up to 2:1 is sufficient, or even up to 1.8:1, or even up to 1.5:1, or even up to 1.3:1, or even up to 1.1:1, or even up to 1:1, or even up to 0.9:1, or even up to 0.8:1. Further examples of ranges include 0.2:1-2:1, or 0.2:1-1.8:1, or 0.2:1-1.5:1, or 0.2:1-1.3:1, or 0.2:1-1.1:1, or 0.2:1-1:1, or 0.2:1-0.9:1, or 0.2:1-0.8:1, or 0.3:1-2:1, or 0.3:1-1.8:1, or 0.3:1-1.5:1, or 0.3:1-1.3:1, or 0.3:1-1.1:1, or 0.3:1-1:1, or 0.3:1-0.9:1, or 0.3:1-0.8:1, or 0.4:1-2:1, or 0.4:1-1.8:1, or 0.4:1-1.5:1, or 0.4:1-1.3:1, or 0.4:1-1.1:1, or 0.4:1-1:1, or 0.4:1-0.9:1, or 0.4:1-0.8:1, or 0.5:1-2:1, or 0.5:1-1.8:1, or 0.5:1-1.5:1, or 0.5:1-1.3:1, or 0.5:1-1:1, or 0.5:1-1:1, or 0.5:1-0.9:1, or 0.5:1-0.8:1, or 0.6:1-2:1, or 0.6:1-1.8:1, or 0.6:1-1.5:1, or 0.6:1-1.3:1, or 0.6:1-1.1:1, or 0.6:1-1:1, or 0.6:1-0.9:1, or 0.6:1-0.8:1. Increasing the wash ratio is one variable for improving the removal of metal catalyst from the dewatered wet cake. Wash ratios in excess of 2:1 can be used if desired.

The temperature of the water wash or wash organic solvent is not limited. Desirably, the wash temperature can range from 60° C. to 120° C., or 60° C. to 110° C., or 60° C. to 100° C., or 60° C. to 90° C., or 60° C. to 80° C., 70° C. to 120° C., or 70° C. to 110° C., or 70° C. to 100° C., or 70° C. to 90° C., or 70° C. to 80° C., or 80° C. to 120° C., or 80° C. to 110° C., or 80° C. to 100° C., or 80° C. to 90° C., or 90° C. to 120° C., or 90° C. to 110° C., or 90° C. to 100° C. Using a hot wash stream 8 aids in the removal of impurities from the dewatered wet cake composition and assists minimizing the moisture content in the washed CCA wet cake.

The wash stream, whether used in a single wash zone or in multiple wash zones, is desirably a single pass wash stream. The single pass wash stream 8 flows through the cake and exits the solid liquid separation device or the process as a wash liquor stream 9. A wash zone desirably does not share a wash stream that has been used in another wash zone before being purified or refined. A wash liquor is not applied to another wash zone without first subjecting the wash liquor to a purification process. The single pass wash stream can be distinguished from, for example, counter-current wash schemes that share a common wash stream in multiple wash zones before being subjected to purification.

The pressure within the wash zone 7 is not limited. Suitable pressures range from 1 to 5 bar gauge, 2 bar to 5 bar, 3 bar to 4 bar gauge. In vacuum filtration, the pressure within the wash zone 7 can range from 0.3 bar absolute to less than 1 bar absolute. The temperature within the wash zone 7 is not limited. Suitable temperatures range from 70° C. to 140° C. The residence time of the dewatered CCA wet cake composition 6 in the wash zone 7 can range from 2 seconds to 60 seconds, from 3 seconds to 30 seconds, from 5 seconds to 20 Seconds, and from 6 seconds to 17. The washed CCA wet cake composition 10 thickness can be from 0.5 inches to 5 inches, or 1 inch to 5 inches, or 2 inches to 5 inches, or 3 inches to 5 inches, or 4 inches to 5 inches.

The wash liquor stream 9 comprises at least a portion mother liquor from the wet cake fed to the wash zone 7, and at least a portion of catalyst metal on the dewatered CCA wet cake 6 fed to the wash zone 7, and optionally solids and optionally a portion of the wash stream 8 fed to the wash zone 7. Each wash zone is fed with a wash solvent (which can be different from wash zone to wash zone). At least some of mobile liquid phase impurities and catalyst metals washed away from the wet cake mother liquor will be present in the wash liquor 9. The wash solvent can comprises acetic acid, water, or any other suitable solvent. The particular wash liquor streams in the process of the invention will depend upon the composition of the liquid phase in the wash zone wet cake, the composition of the wash solvent, and the amount of wash solvent used.

For example, if the mass of wash solvent 9 fed to the wash zone 7 is less than the mass of mother liquor liquid present in wet cake fed to the wash zone 7, the wash liquor will comprise 100% mother liquor. The wash solvent 8 serves to displace mother liquor in the wet cake but can be present in insufficient quantities to pass through the wet cake and exit into the wash liquor. However, if the mass of wash solvent 8 routed to the wash zone is more than the mass of mother liquor in wet cake fed to the wash zone 7, the wash liquor 9 comprises a mixture of mother liquor and wash solvent.

Desirably, the washed CCA wet cake composition proceeds to cake discharge zone (not shown in the figures), where the washed CCA wet cake composition is removed from the solid liquid separation device, and more particularly, removed from a filter cloth. The washed CCA wet cake composition can be removed from the filter cloth by a knife, or a back pulse of gas, or by any other means known in the art. Another feature of the invention includes a process for discharging a washed CCA wet cake composition from a filter cloth using a stream of water. The water can be applied to the surface of the wet cake, such as by spray, to erode the wet cake from a cake discharge zone. When the wet cake is sufficiently eroded, the water application, if continued, can contact the filter media so that the filter media is at least partially washed by the water application This feature has the advantage of simultaneously washing (at least partially) the filter cloth and discharging the washed CCA wet cake composition from the cake discharge zone. This also has the advantage of reducing the amount of downstream wash needed to wash the filter media before it is fed back to the filter cake formation zone, or even a downstream wash zone that remove all solids from the filter media can be eliminated altogether by using a water spray in the cake discharge zone.

Optionally, a back blow of gas can be applied to the filter media during at least a portion of the water spray application to assist in discharging the wet cake from the filter media. Or if desired, a back flow of water, through the surface of the filter media opposite to the surface contacting the washed CCA wet cake composition, can be applied to assist in the removal of the CCA wet cake composition from the filter media. This feature has the advantage in assisting the water spray operation to simultaneously wash of the filter media and discharge the washed CCA wet cake composition from the discharge zone.

The stream of discharged washed CCA wet cake composition, now a combination of CCA solids and water, then drops into a tank where more water can, if desired, be added to generate a pumpable aqueous slurry that is optionally fed indirectly or directly to a hydrogenation unit.

When the washed CCA wet cake composition is fed to a hydrogenation unit it can be desirable to have removed as much of the organic solvent as possible. In one embodiment the dewater and subsequent wash steps of the present invention allow production of a washed CCA wet cake composition to possess very low levels of the organic solvent even without the process including a predominantly evaporative drying process. As used throughout this application, a "predominantly evaporative drying process" is a process in which liquids are removed from a composition and in which at least about 80% of the liquids removed are removed by evaporation (and not, for example, by physical displacement). In some embodiments, a predominantly evaporative drying process can be a process in which at least about 85%, at least about 90%, at least about 95%, at least about 97.5% or at least about 99% of the liquids removed are removed by evaporation. Thus, in some embodiments, the combination of wash and dewater allows the washed CCA wet cake composition contains no more than about 100 ppm organic solvent by weight even though the process does not include a predominantly evaporative drying process. In some embodiments, the amount of organic solvent can be no more than about 75 ppm, no more than about 50 ppm, no more than about 25 ppm, no more than about 5 ppm or no more than about 1 ppm.

Some examples of processes that can be operated as predominantly evaporative drying processes include indirect heating (e.g. by contact with a surface heated to a temperature at least about 5° C. higher than that of the composition being heated), direct heating (e.g. by contact with a fluidized medium heated to a temperature at least about 5° C. higher than that of the composition being heated). Thus, the invention can also produce washed CCA wet cake composition to possess contains no more than about 100 ppm organic solvent by weight even though the process does not include a process in which a composition is contacted with either a fluidized medium or surface heated to a temperature at least about 5° C. higher than that of the composition. In some embodiments the temperature is at least about 10° C., at least about 15° C., at least about 20° C., at least about 25° C., at least about 30° C., at least about 40° C., or at least about at least about 50° C. higher than that of the composition being heated than that of the composition being heated. In some embodiments at each of these temperature ranges, the amount of organic solvent is no more than about 75 ppm, no more than about 50 ppm, no more than about 25 ppm, no more than about 5 ppm or no more than about 1 ppm by weight.

One or more of the filter cake formation zone 1, the dewatering zone 4, and the wash zone 7 can be contained in separate devices or housings, or can defined within a single solid/liquid separation device or housing (e.g. single continuous filter). For example, all of the above mentioned zones 1, 4, and 7 can be defined within a single rotary pressure drum filter. Alternatively, these zones can be defined within a continuous vacuum belt filter.

The step of dewatering is performed before the final wash step. By performing a dewatering step before the final wash step, the amount of impurities such as cobalt that are removed are increased to generate a final product, whether a washed CCA wet cake composition 10 or a low moisture washed CCA wet cake as explained below, with lower amounts of residual impurities, and in particular, a lower amount of cobalt metal as compared to a process with the same number of steps but in which the wash step is performed prior to the first dewatering step.

It is desired to remove as much catalyst metal or other impurities from the CCA composition because some metals and impurities adversely affect the formation of a low color, transparent, high yielding polyester polymer with low acetaldehyde forming precursors. It is also desirable to remove as much catalyst metal and other impurities, and in particular cobalt, from the CCA composition in order to recover cobalt, for recycling to the primary oxidation reactor for re-use in oxidation reactions, due to the expense of cobalt and other catalyst metals. The process of the invention allows one to increase the recovery of cobalt metal in one or more of the first mother liquor stream, the second mother liquor stream, and the wash stream and recycle the stream directly or indirectly to a catalyst mix tank for feeding the primary oxidation reactor or directly or indirectly to the primary oxidation reactor.

The total residence time of the CCA composition in the filter cake formation zone, the CCA wet cake composition in the dewatering zone, the dewatered wet cake composition in the wash zone, and discharge of the washed CCA wet cake composition is not limited, and can be up to 1 hour, but is desirably 5 minutes or less, or 4 minutes or less, or 3 minutes or less, or 1.5 minutes or less, or 1 minute or less, and for each of these upper limits on residence time, the cumulative residence time can be as fast as at least 30 seconds.

Figure 4:
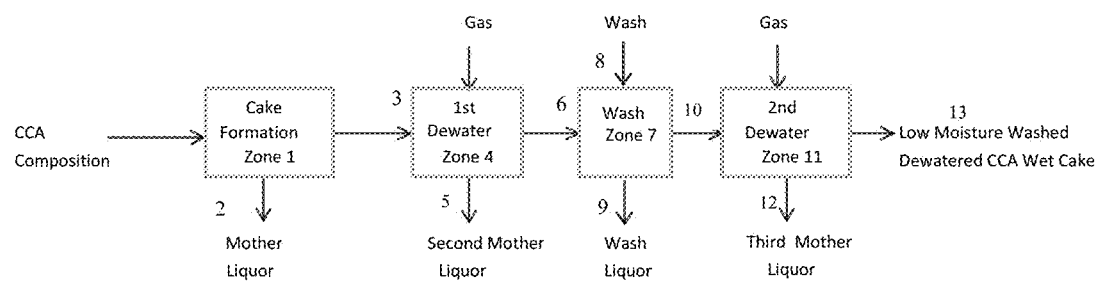
FIG. 4 is a block flow diagram of a process of the invention having multiple dewatering steps, with a dewatering step preceding a wash step.
Figure 5:
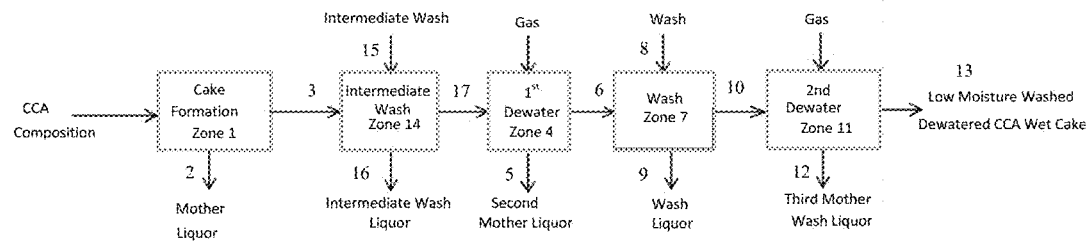
FIG. 5 is a block flow diagram of a process of the invention having multiple wash and multiple dewatering steps, with a dewatering step preceding a wash zone.

The process of the invention includes a variety of configurations, provided that a dewatering step is performed before the final wash step. For example, multiple dewatering zones can be provided as illustrated in FIG. 4, and a combination of multiple wash zones and multiple dewatering zones can be provided as illustrated in FIG. 5. The additional wash zones and dewatering zones can be located in any sequence desired, so long as at least one dewatering step is performed prior to the last wash step. Thus, although the process of the invention includes at least a dewatering step before a wash step, any number of additional wash steps and zones and any number of dewatering steps or zones can be added, provided that before a final wash step is performed, at least one dewatering step is included and performed.

As illustrated in FIG. 4, an optional additional dewatering zone 11 or step can be added after the wash zone 7. The washed CCA wet cake composition 10 is fed to second dewatering zone 11 to generate a third mother liquor composition in stream 12 and a low moisture washed CCA wet cake composition 13. The weight percent of liquid (including moisture) level in the low moisture washed CCA wet cake composition 13 is lower that the weight percent of liquid in the washed CCA wet cake composition 10. This dewatering step aids in removing liquids from the wet cake so that the energy consumption of a downstream predominantly evaporative drying process is reduced.

To conduct dewatering in the second dewatering zone 11, the washed CCA wet cake composition 10 fed to the second dewater zone 11 is contacted with a stream of gas. The gas stream can be the same or different from the gas stream fed to the first dewatering zone 4. For example the gas stream fed to the second dewatering zone comprises an inert gas or air. The gas can be dried prior to its introduction into the dewatering zone. The gas can comprise greater than 90 wt. % nitrogen based on the weight of the introduced gas. The flow rate of the gas stream fed to the second dewatering zone 11 can be 0.4-1.4 L/min/cm². The pressure in the second dewatering zone 11 can be 1-5 bar. The gas temperature can be from 60° C. to 140° C.

The direction at which the gas is set to flow is not limited. Gas flow can be substantially perpendicular to the direction of the filter media to improve the efficiency of removing liquid from the washed CCA wet cake composition 10.

A third mother liquor stream 12 is discharged from the second dewatering zone 11. The third mother liquor composition in stream 12 discharged from the dewatering zone 11 can comprise organic solvent, water, one or more catalyst components, oxidation byproducts, or dissolved DCA, or a combination of any of the foregoing, and optionally can contain dissolved or entrained gas from the gas feed to the second dewatering zone 11. The third mother liquor composition 12 can comprise organic solvent or water in an amount of at least 85 weight percent, at least 95 weight percent, or at least 99 weight percent, based on the weight of the third mother liquor composition in stream 12.

The catalyst components in the third mother liquor 12 can comprise the catalyst components as described above with reference to the catalyst system introduced into the oxidation reactor (e.g., cobalt, manganese, and/or bromine). The third mother liquor composition 12 can have a cumulative concentration of all of the catalyst components in the range of from 0 to 5,000 ppmw, in the range of from 20 to 3,000 ppmw, or in the range of from 20 to 1,000 ppmw, based on the weight of the third mother liquor stream 12. The cumulative amount of metals, or the amount of cobalt metal, in the third mother liquor stream 12 are desirably less than the respective cumulative amount of metals, or the amount of cobalt, in the second mother liquor stream 5 withdrawn from the first dewatering zone 4.

The third mother liquor stream 12 can contain at least a portion of the gas fed to the second dewatering zone 11, and optionally the entire gas stream fed to the second dewatering zone 11. The third mother liquor stream 12 can comprise a liquid/gas phase, wherein at least a portion of the gas phase is the gas fed to the dewatering zone. The amount of gas contained in the third mother liquor stream 12 can be less than 10%, less than 5%, less than 3%, less than 1%, less than 0.5%, on a mass basis, based on the weight of the third mother liquor stream 12.

The third mother liquor composition in stream 12 discharged from the dewatering zone 11 can comprise solids in an amount of less than 1 weight percent, or less than 0.5 weight percent, or less than 0.1 wt. %, or less than 0.05 wt. %, or less than 0.01 wt. %. Additionally, the third mother liquor composition 12 can have a temperature of less than 200° C., or in the range of from 20° C. to 150° C., or in the range of from 20° C. to 70° C.

The liquid volume of the third mother liquor stream 12 can be the same as or less than the liquid volume of the second mother liquor stream 5.

The pressure within the second dewatering zone is not limited. Suitable pressures range from 1 to 5 bar gauge, 2 bar to 5 bar gauge, 3 bar to 4 bar gauge. In vacuum filtration, the pressure within the filter cake formation zone 1 can range from 0.3 bar absolute to less than 1 bar absolute The temperature within the dewatering zone is not limited. Suitable temperatures range from 70° C. to 140° C. The residence time of the washed CCA wet cake composition 10 to its transformation into the low moisture washed dewatered CCA wet cake composition 13 in the second dewatering zone 11 can range from 2 seconds to 60 seconds, from 3 seconds to 30 seconds, from 5 seconds to 20 seconds, and from 6 seconds to 17. The thickness of the low moisture washed CCA wet cake composition 13 can be from 0.5 inches to 5 inches, or 1 inch to 5 inches, or 2 inches to 5 inches, or 3 inches to 5 inches, or 4 inches to 5 inches.

If desired, an intermediate wash zone 14 can be added as illustrated in FIG. 5. The CCA wet cake composition 3 is fed to the intermediate wash zone 14 to generate an intermediate wash liquor 16 and an intermediate washed CCA wet cake composition 17 that is fed to the first dewatering zone 4.

In the intermediate wash zone 14, the CCA wet cake composition 3 is contacted with an intermediate wash stream 15 fed to the intermediate wash zone 14 that contacts the CCA wet cake composition 3. The intermediate wash stream 15 can be water, an organic solvent, or a mixture thereof. Desirably, the concentration of organic solvent in the wash stream 15, such as acetic acid, is at least 50 wt. %, or at least 60 wt. %, or at least 70 wt. %, or at least 80 wt. %, or at least 90 wt. %, or at least 95 wt. %, or at least 98 wt. %, or at least 99 wt. %, based on the weight of the feed of wash stream 15.

The amount of wash organic solvent fed to the intermediate wash zone 14 is not limited. The amount of wash stream 15 fed to the intermediate wash zone 14 is desirably at a wash ratio (defined as the mass of wash/mass of dry solids in the dewatered wet cake composition 6) from at least 0.2:1, or at least 0.3:1, or at least 0.4:1, or at least 0.5:1, or at least 0.6:1. There is no particular upper limit, but for economy, a wash ratio of up to 2:1 is sufficient, or even up to 1.8:1, or even up to 1.5:1, or even up to 1.3:1, or even up to 1.1:1, or even up to 1:1, or even up to 0.9:1, or even up to 0.8:1. Further examples of ranges include 0.2:1-2:1, or 0.2:1-1.8:1, or 0.2:1-1.5:1, or 0.2:1-1, 3:1, or 0.2:1-1.1:1, or 0.2:1-1:1, or 0.2:1-0.9:1, or 0.2:1-0.8:1, or 0.3:1-2:1, or 0.3:1-1.8:1, or 0.3:1-1.5:1, or 0.3:1-1.3:1, or 0.3:1-1.1:1, or 0.3:1-1:1, or 0.3:1-0.9:1, or 0.3:1-0.8:1, or 0.4:1-2:1, or 0.4:1-1.8:1, or 0.4:1-1.5:1, or 0.4:1-1.3:1, or 0.4:1-1.1:1, or 0.4:1-1:1, or 0.4:1-0.9:1, or 0.4:1-0.8:1, or 0.5:1-2:1, or 0.5:1-1.8:1, or 0.5:1-1.5:1, or 0.5:1-1.3:1, or 0.5:1-1.1:1, or 0.5:1-1:1, or 0.5:1-0.9:1, or 0.5:1-0.8:1, or 0.6:1-2:1, or 0.6:1-1.8:1, or 0.6:1-1.5:1, or 0.6:1-1.3:1, or 0.6:1-1.1:1, or 0.6:1-1:1, or 0.6:1-0.9:1, or 0.6:1-0.8:1. Increasing the wash ratio is one variable for improving the removal of metal catalyst from the dewatered wet cake. Wash ratios in excess of 2:1 can be used if desired.

The temperature of the intermediate wash stream 15 is not limited. Desirably, the wash temperature can range from 60° C. to 120° C., or 60° C. to 90° C., or 60° C. to 80° C. Using a hot wash stream 15 aids in the removal of impurities from the CCA wet cake composition.

The pressure within the intermediate wash zone 14 is not limited. Suitable pressures range from 1 to 5 bar gauge, 2 bar to 5 bar, 3 bar to 4 bar gauge. The temperature within the intermediate wash zone 14 is not limited. Suitable temperatures range from 70° C. to 140° C. The residence time of the CCA wet cake composition 3 in the intermediate wash zone 14 can range from 2 seconds to 60 seconds, from 3 seconds to 30 seconds, from 5 seconds to 20 seconds, and from 6 Seconds to 17. The intermediate washed CCA wet cake composition 17 thickness can be from 0.5 inches to 5 inches, or 1 inch to 5 inches, or 2 inches to 5 inches, or 3 inches to 5 inches, or 4 inches to 5 inches.

The intermediate wash liquor stream 16 comprises at least a portion of the mother liquor present in the CCA wet cake 3 fed to the intermediate wash zone 14, and optionally solids and a portion of the intermediate wash stream 15 fed to the intermediate wash zone 14.

The intermediate wet cake composition 17 thickness can be from 0.5 inches to 5 inches, or 1 inch to 5 inches, or 2 inches to 5 inches, or 3 inches to 5 inches, or 4 inches to 5 inches. The intermediate CCA wet cake composition 17 comprises DCA solids and a portion of the wash stream solvent along with any other impurities and catalyst metals remaining after the wash. The intermediate CCA wet cake composition 17 is fed to a first dewatering zone 4 as shown in FIG. 5. The remainder of the process steps in the configuration illustrated in FIG. 5 is as described in FIG. 4, and that the concentrations of impurities and catalyst metals in each of the subsequent mother liquor streams and wash liquors and resulting cakes will be lower than a comparable configuration without the intermediate wash zone 14.

Figure 6:
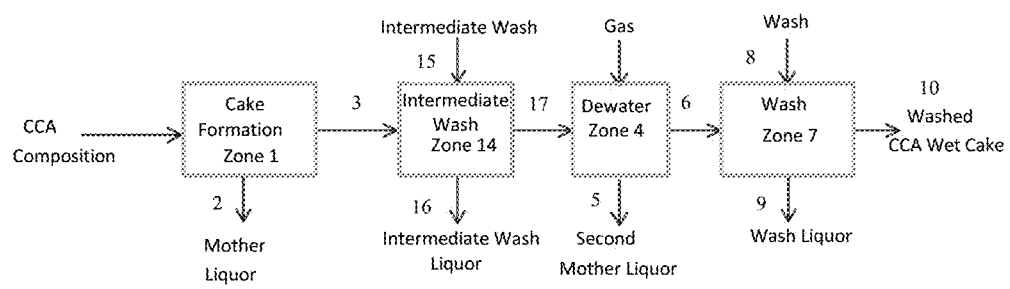
FIG. 6 is a block flow diagram of a process of the invention having multiple wash steps, with a dewatering step preceding a wash zone.

FIG. 6 illustrates an additional configuration of the invention. The configuration of FIG. 6 is the same as that of FIG. 5, except that the final dewatering step of FIG. 5 is not present in the configuration of FIG. 6. The configuration of FIG. 5 has the advantage in that capital and operating costs are not incurred in a final dewatering step, and this configuration can be utilized, for example, when it is not necessary to provide for a low moisture content final wet cake composition. For example, if the final wet cake composition will be fed to a hydrogenation zone, it is not necessary to obtain a low moisture wet cake because the wet cake is typically slurried in water as a proper feed to the hydrogenation zone. Thus, the washed CCA wet cake 10 can have a high level of moisture, yet be purified of catalyst metals to a level lower than that of the configuration in FIG. 3 because of the addition of an intermediate wash zone 14.

The figures illustrate only some examples of the many possible configurations for making a washed CCA wet cake or a low moisture washed CCA wet cake. For example, more than 2 wash steps can be provided at any point in the process, and more than 2 dewatering steps can be provided at any point in the process, and each of these may be placed in any sequence, such as 2 or more dewatering steps back to back, 2 or more wash steps back to back, in a staggered configuration, or a combination of back to back and staggering (e.g. wash-wash-dewater-wash; dewater-dewater-wash; dewater-dewater-wash-wash; wash-dewater-wash-wash; etc.), so long as in each case, there is a dewatering step provided before a final wash, and desirably, a dewatering step provided before a second wash if more than one wash step is used.

One or more of the filter cake formation zone, one or more of the dewatering zones, and one or more of the wash zones can be contained in separate devices or housings, or can defined within a single solid/liquid separation device or housing. For example, all of the above mentioned zones can be defined within a single rotary pressure drum filter.

As a result of the process of the invention, there is also provided a washed CCA wet cake composition and a low moisture washed CCA wet cake composition having a low amount of cobalt, on the order of 50 ppm or less, or 40 ppm or less, or 30 ppm or less, or 25 ppm or less, or 20 ppm or less, and in each case 5 ppm or more, using only one dewatering step at a wash ratio of less than 1:1. With two dewatering steps, one may obtain a low moisture washed CCA wet cake composition having an amount of cobalt on the order of 20 ppm or less, or 15 ppm or less, or 10 ppm or less, or 9 ppm or less, or 8 ppm or less, or 7 ppm or less, of 6 ppm or less, or 5 ppm or less, and in each case at undetectable levels or at amounts of 0 ppm or more (meaning that the amounts if any would be in the parts per billion range), or at amounts of 1 ppm or more.

As a result of the process of the invention, there is also provided a washed CCA wet cake composition and a low moisture washed CCA wet cake composition having a low amount of cobalt, on the order of 30 ppm or less, or 25 ppm or less, or 20 ppm or less, or 15 ppm or less, or 12 ppm or less, or 10 ppm or less, utilizing only 2 or less wash steps.

In each of the above cases, the low cobalt results can be achieved at a low wash ratio of 0.3:1 to 2:1, or 0.3:1 to 1:1, or 0.3:1 to 0.5:1.

By conducting a dewatering step on the wet cake before a final cake wash step, the amount of catalyst removed is increased. Optionally, if desired, the same amount of catalyst or high amounts of catalyst can be retained on the wet cake while reducing the amount of wash acid used to wash the wet cake. By reducing the amount of wash acid used, the amount of organic solvent present in the wash stream is also reduced. This provides the advantage in that energy or smaller equipment is needed to recover the organic solvent. For example, there is provided a step comprising feeding one or more of the wash liquor streams to a waste water treatment facility directly or indirectly without the use of a distillation column prior to introducing the wash liquor stream to the quiescent basin or a water borne micro-organism habitat in a waste water treatment facility.

If a dewatering step is provided after the last wash step, it is also now possible to provide a moisture content sufficiently low, without a predominantly evaporative drying process, in a low moisture washed CCA wet cake composition. For example, some predominantly evaporative drying processes apply heat energy sufficient to evaporate moisture, with at least 60 wt. %, or at least 70 wt. %, or at least 75 wt. %, or at least 80 wt. %, or at least 85 wt. %, or at least 90 wt. %, or at least 95 wt. %, or at least 96 wt. %, or at least 97 wt. %, or at least 98 wt. %, or at least 98.5 wt. %, or at least 99 wt. %, or at least 99.5 wt. % of the moisture present on the low moisture washed CCA wet cake being removed. There can be provided a low moisture washed CCA wet cake composition 13 having a moisture content, without a predominantly evaporative drying process, of 35 wt. % or less, or 33 wt. % or less, or 32 wt. % or less, or 31 wt. % or less, or 30 wt. % or less, or 28 wt. % or less, or 27 wt. % or less, or 26 wt. % or less, or 25 wt. % or less, or 23 wt. % or less, or 21 wt. % or less, or 20 wt. % or less, or 18 wt. % or less, or 17 wt. % or less, or 15 wt. % or less, or 12 wt. % or less, in each case based on the weight of the low moisture washed CCA wet cake composition. By this technique, a process can now be provided which does not include a predominantly evaporative drying process for the filter cake before creating a water slurry feed to a hydrogenation zone. If desired, by the process of the invention, one may discharge the CCA wet cake composition from a filter cloth with a water wash and thereby simultaneously wash the filter cloth with the same water wash.

Even if a dewatering step is not used to reduce levels of moisture after the final wash step, the use of one or more dewatering step(s) prior to the final wash step allows the production of a CCA wet cake composition having low levels of the organic solvent despite having a fairly high moisture content. Thus, in some embodiments, the washed CCA wet cake composition contains no more than about 100 ppm by weight organic solvent by weight even though it also contains it contains at least about 5 wt. % moisture. In some embodiments, the amount of organic solvent can be no more than about 75 ppm, no more than about 50 ppm, no more than about 25 ppm, no more than about 5 ppm or no more than about 1 ppm at moisture levels of at least about 5 wt. %. Embodiments exist for each of the foregoing levels of organic solvent at moisture levels of at least about 10 wt. %, at least about 15 wt. %, at least about 20 wt. %, at least about 25 wt. % and at least about 30 wt. %.

The following examples illustrate one or more configurations and the advantages of the invention.

EXAMPLES

Each of the following Examples were conducted in a 1-liter, jacketed, pressure pocket filter manufactured by BHS Filtration Company. The filter was fitted with a 43 micron metal cloth with a filtration area of 20 cm². Crude isophthalic acid (IPA) prepared using a cobalt catalyst system and having a mean particle size of about 110 microns was slurried in acetic acid to generate feed slurry containing about 30 wt. % solids and a temperature of about 75 C. The nominal slurry charge was about 535 g, resulting in a 4 inch nominal cake height. Dry pressurized nitrogen was used as the motive force for filtration, washes, and dewatering steps. Wet cake analyses were made by wavelength dispersive X-ray fluorescence (WDXRF) analysis to determine residual cobalt in the cakes. A sample of each cake was also subjected to moisture analysis using an Arizona Instruments CompuTrac Max200 Moisture Analyzer to determine the cake wetness (% liquor).

Comparative Example 1

Filter Zone, Acid Wash Zone, Dewater Zone

The top of the filter was opened and feed slurry was added. The top of the filter was closed and the filter was pressurized to 60 psig. The bottom filter valve was opened for 11 seconds and then closed allowing mother liquor to exit the filter for 11 seconds, forming a filter cake in the filter. The resulting filter cake in the filter had an observable liquid level above the top of the wet cake, but the liquid level was no more than 0.5 inches above the top of cake. The filter was slowly depressurized to ambient pressure.

The top of the filter was opened and acetic acid wash was added. The amount of wash added in this example was about 0.6:1 ratio of wash mass to dry solids mass (i.e. a wash ratio of about 0.6). The top of the filter was then closed and the filter was pressurized to 60 psig. The bottom filter valve was opened allowing wash liquor to exit the filter.

The bottom valve remained open long enough to dewater the cake. Dewatering was identified by observation of gas breakthrough (a visible interruption in the continuous flow of wash liquor). Dewatering of the cake was allowed to continue for 8 seconds after gas breakthrough was observed. Washed and dewatered wet cakes were removed from the filter for analysis. Results are in Table 1:

TABLE 1

Cobalt Displacement by Single Stage
Acid Washing of Isophthalic Acid

| Run No. | Wash Acid Mass Ratio | Cake Dryness, % solids | Residual Cobalt in Cake, ppm |
| --- | --- | --- | --- |
| 1 | 0.60 | 81% | 110 |
| 2 | 0.64 | 82% | 86.4 |
| 3 | 0.63 | 83% | 109 |
| 4 | 0.63 | 84% | 77.9 |
| 5 | 0.61 | 83% | 96.9 |

Example 2

Filter Zone, Dewater Zone, Acid Wash Zone, Dewater Zone

The top of the filter was opened and feed slurry was poured into the filter. The top of the filter was closed and the filter was pressurized to 60 psig. The bottom filter valve was opened, allowing flow of mother liquor out of the filter, but unlike Comparative Example 1, the cake was dewatered by allowing flow to continue until gas breakthrough was observed and the bottom valve was then closed resulting in a dewatered cake in the filter. The filter was depressurized.

The top of the filter was opened and acetic acid wash was added. The amount of wash added in this example ranged from 0.2:1 to 1.4:1 (ratio of wash mass to dry solids mass). The top of the filter was then closed and the filter was pressurized to 60 psig. The bottom filter valve was opened, allowing wash liquor to exit the filter.

The cake was dewatered by keeping the bottom valve open until gas breakthrough was observed and for 10 seconds after gas breakthrough. Washed and dewatered wet cakes were removed from the filter for analysis. Results are in Table 2.

TABLE 2

Cobalt Displacement by Single Stage Acid Washing of Isophthalic
Acid Preceded by Filtration to the Point of Breakthrough

| Run No. | Filtration Time to Breakthrough, (sec) | Wash Ratio (g wash/g solid) | Cake Dryness, % solids | Residual Cobalt in Cake, ppm |
| --- | --- | --- | --- | --- |
| 6 | 10.7 | 0.2 | 88% | 96.8 |
| 7 | 10.2 | 0.4 | 89% | 30.8 |
| 8 | 10.7 | 0.5 | 89% | 23 |
| 9 | 10.9 | 0.7 | 88% | 10.9 |
| 10 | 11.2 | 0.9 | 89% | 18 |
| 11 | 11.9 | 1.2 | 89% | 15.7 |
| 12 | 12.8 | 1.4 | 89% | 13.8 |

Comparative Example 3

Filter Zone, $1^{st}$ Wash-Acid, $2^{nd}$ Wash-Acid, Dewater Zone

The top of the filter was opened and feed slurry was added. The top of the filter was closed and the filter was pressurized to 60 psig. The bottom filter valve was opened for 11 seconds and then closed allowing mother liquor to exit the filter for 11 seconds, forming a filter cake in the filter. The resulting filter cake in the filter had an observable liquid level above the top of wet cake, but the liquid level was no more than 0.5 inches above the top of the cake. The filter was slowly depressurized to ambient pressure.

The top of the filter was opened and a $1^{st}$ acetic acid wash was added. The amount of wash added in this example was about 0.4:1 ratio of wash mass to dry solids mass (i.e. a wash ratio of about 0.4). The top of the filter was then closed and the filter was pressurized to 60 psig. The bottom filter valve was opened allowing a $1^{st}$ wash liquor to exit the filter. The resulting once washed filter cake in the filter had an observable liquid level above the top of the wet cake, but the liquid level was no more than 0.5 inches above the top of the cake. The filter was slowly depressurized to ambient pressure.

The top of the filter was opened and a $2^{nd}$ acetic acid wash was added. The amount of $2^{nd}$ wash added in this example was about 0.4:1 ratio of wash mass to dry solids mass (i.e. a wash ratio of about 0.4). The top of the filter was then closed and the filter was pressurized to 60 psig. The bottom filter valve was opened, allowing a 2nd wash liquor to exit the filter.

The cake was dewatered by keeping the bottom valve open until gas breakthrough was observed. The valve was kept open for 8 seconds after gas breakthrough. Twice consecutively washed and dewatered wet cakes were removed from the filter for analysis. Details are in Table 3:

TABLE 3

Cobalt Displacement by Two Stages
of Acid Washing of Isophthalic Acid

| Run No. | First Wash Acid Mass Ratio | Second Wash Acid Mass Ratio | Cake Dryness, % solids | Residual Cobalt in Cake, ppm |
| --- | --- | --- | --- | --- |
| 13 | 0.39 | 0.38 | 83% | 22.9 |
| 14 | 0.37 | 0.36 | 84% | 22.8 |
| 15 | 0.38 | 0.39 | 82% | 28.1 |
| 16 | 0.44 | 0.44 | 83% | 23 |
| 17 | 0.45 | 0.45 | 83% | 19.1 |
| 18 | 0.46 | 0.45 | 84% | 19.6 |

Example 4

Filter Zone, 1$^{st}$ Wash-Acid, 1$^{st}$ Dewater, 2$^{nd}$ Acid Wash-Acid, 2$^{nd}$ Dewater The top of the filter was opened and feed slurry was added. The top of the filter was closed and the filter was pressurized to 60 psig. The bottom filter valve was opened for 11 seconds and then closed allowing mother liquor to exit the filter for 11 seconds, forming a filter cake in the filter. The resulting filter cake in the filter had an observable liquid level above the top of the wet cake but the liquid level was no more than 0.5 inches above the top of the cake. The filter was slowly depressurized to ambient pressure.

The top of the filter was opened and a 1$^{st}$ acetic acid wash was added. The amount of 1$^{st}$ wash added in this example ranged from about 0.34:1 to about 1.07:1 ratio of wash mass to dry solids mass. The top of the filter was then closed and the filter was pressurized to 60 psig. The bottom filter valve was opened allowing a 1$^{st}$ wash liquor to exit the filter.

The cake was dewatered by keeping the bottom valve open until gas breakthrough was observed. Dewatering of the cake was allowed to continue by keeping the valve open for 5 seconds after gas breakthrough, resulting in a once washed and dewatered wet cake remaining in the filter. The filter was slowly depressurized to ambient pressure.

The top of the filter was opened and a 2$^{nd}$ acetic acid wash was added. The amount of 2$^{nd}$ wash added ranged from 0.19:1 to 0.97:1 ratio of wash mass to dry solids mass. The top of the filter was then closed and the filter was pressurized to 60 psig. The bottom filter valve was opened allowing wash a 2d wash liquor to exit the filter.

The cake was dewatered by keeping the bottom valve open until gas breakthrough was observed. Dewatering of the cake was allowed to continue by keeping the valve open for 10 seconds after gas breakthrough. Wet cakes were removed from the filter for analysis. Results are in Table 4:

TABLE 4

Cobalt Displacement by Two Stages of Acid Washing of Isophthalic Acid with an Intermediate Drying Stage

| Run No. | First Wash Acid Mass Ratio | Second Wash Acid Mass Ratio | Cake Dryness, % solids | Residual Cobalt in Cake, ppm |
|---|---|---|---|---|
| 19 | 0.34 | 0.25 | 83% | 6.2 |
| 20 | 0.43 | 0.43 | 82% | 8.4 |
| 21 | 0.54 | 0.36 | 85% | 5.6 |
| 22 | 0.76 | 0.19 | 86% | 6.5 |
| 23 | 0.49 | 0.97 | 86% | 5.3 |
| 29 | 0.96 | 0.48 | 88% | 6.6 |
| 32 | 1.07 | 0.27 | 86% | 5.4 |
| 34 | 0.45 | 0.23 | 87% | 7.0 |
| 35 | 0.37 | 0.37 | 88% | 5.4 |

Figure 7:
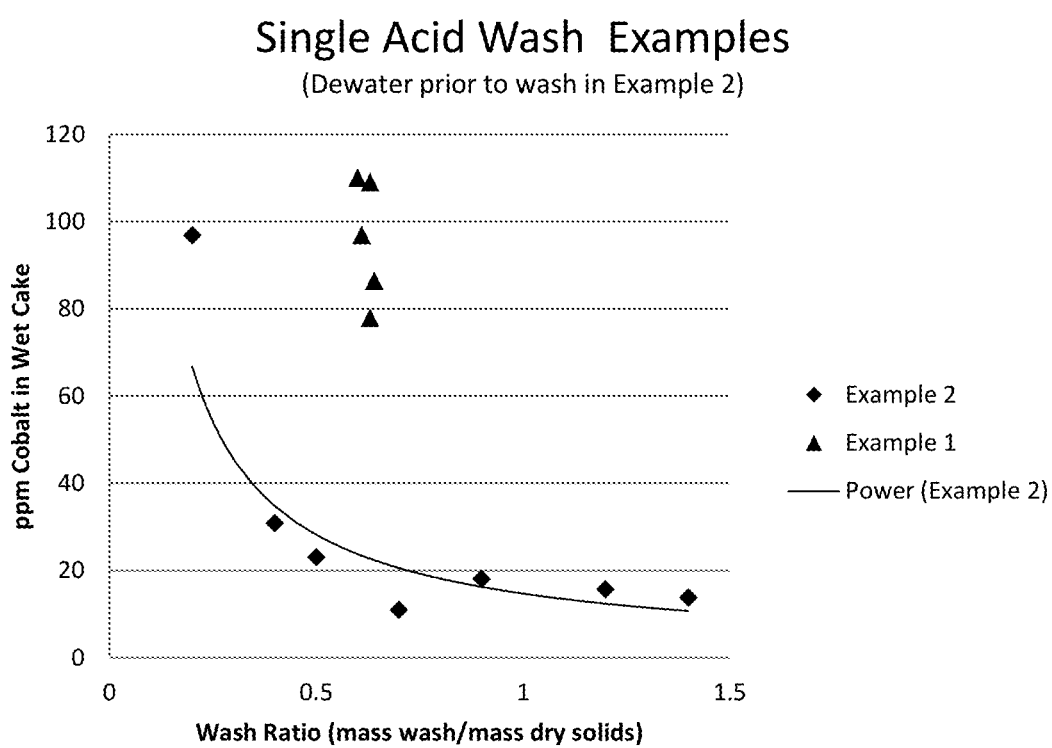
FIG. 7 is a graph illustrating the amount of cobalt remaining in a wet cake at a variety of wash ratios for single wash example.
Figure 8:
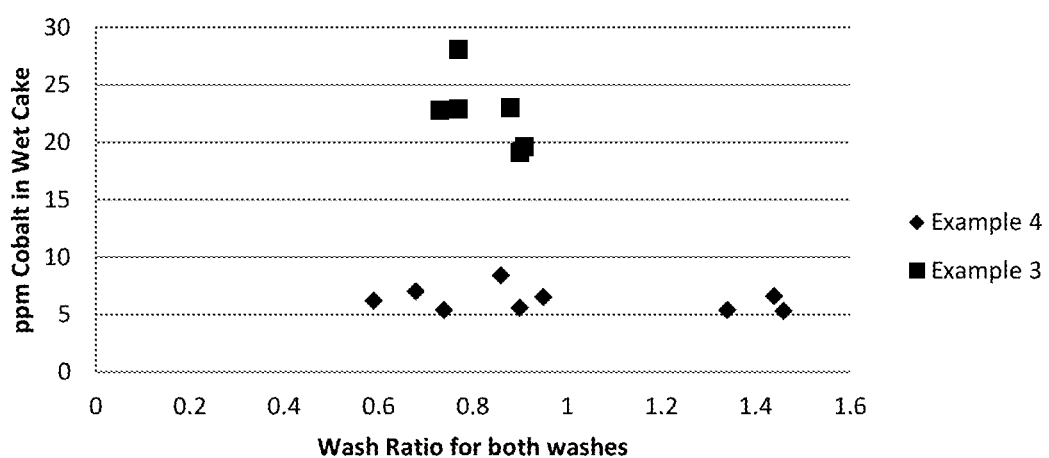
FIG. 8 is a graph illustrating the amount of cobalt remaining in a wet cake at a variety of wash ratios for a double wash event with a dewatering step preceding a final wash step.

A summary of the results from Examples 1-4 and their runs above are graphically represented in FIGS. 7 and 8.

FIG. 7 illustrates that at a given wash ratio and a single wash, the amount of cobalt removed by including a dewatering step is dramatically increased. While low amounts of cobalt can be achieved in two wash steps without dewatering, the use of two wash steps increases the amount of organic solvent that must be recovered relative to one wash step with a dewatering step.

FIG. 8 graphically illustrates that if a two wash step configuration is acceptable, the addition of a dewatering step before the final wash step can increase the amount of cobalt removed by more than 100% at equivalent wash ratios.

Example 5

Filter, 1$^{st}$ Wash-Acid, Dewater, 2$^{nd}$ Wash-Water, Dewater

This example demonstrates the ability to eliminate acetic acid and achieve excellent cobalt washing from an isophthalic acid wet cake by employing a dewater step prior to a final wash zone using water as the wash solvent.

The top of the filter was opened and feed slurry was added. The top of the filter was closed and the filter was pressurized to 60 psig. The bottom filter valve was opened for 11 seconds and then closed, allowing mother liquor to exit the filter for 11 seconds, forming a filter cake in the filter. The resulting filter cake in the filter had observable liquid above the top of the wet cake, but the liquid level was no more than 0.5 inches above the top of the cake. The filter was slowly depressurized to ambient pressure.

The top of the filter was opened and a 1$^{st}$ wash was added using acetic acid as the wash solvent. The amount of 1$^{st}$ wash added in this example ranged from about 0.46:1 to about 0.75:1 ratio of wash mass to dry solids mass. The top of the filter was then closed and the filter was pressurized to 60 psig. The bottom filter valve was opened, allowing a 1$^{st}$ wash liquor to exit the filter.

The cake was dewatered by keeping the bottom valve open until gas breakthrough was observed. The bottom valve was kept open for 10 seconds after gas breakthrough resulting in a once acid washed and dewatered wet cake remaining in the filter. The filter was slowly depressurized to ambient pressure.

The top of the filter was opened and a 2$^{nd}$ wash was added using water as the wash solvent. The amount of 2$^{nd}$ wash added ranged from 0.81:1 to 1.17:1 ratio of wash mass to dry solids mass. The top of the filter was then closed and the filter was pressurized to 60 psig. The bottom filter valve was opened allowing wash a 2d wash liquor comprising water to exit the filter.

The cake was dewatered by keeping bottom valve open until gas breakthrough was observed. Dewatering of the cake was allowed to continue for 10 seconds after gas breakthrough. Wet cakes were removed from the filter for analysis. Results are presented in Table 5.

TABLE 5

Cobalt and Acetic Acid Displacement from Isophthalic Acid Cake through a Single Acid Wash Followed by Dewatering Followed by a Single Water Wash

| Run No. | Wash Acid Mass Ratio | Wash Water Mass Ratio | Cake Dryness, % solids | Residual Cobalt in Cake, ppm | Water-Excluded Residual Acetic Acid in Cake, wt. % |
|---|---|---|---|---|---|
| 36 | 0.46 | 0.81 | 69% | <5.0 | 0.010 |
| 37 | 0.47 | 0.96 | 66% | <5.0 | 0.007 |
| 38 | 0.47 | 1.13 | 66% | <5.0 | 0.005 |
| 39 | 0.59 | 0.82 | 66% | <5.0 | 0.003 |
| 40 | 0.60 | 0.99 | 65% | <5.0 | 0.006 |
| 41 | 0.61 | 1.17 | 65% | <5.0 | 0.003 |
| 42 | 0.75 | 0.87 | 66% | <5.0 | 0.005 |
| 43 | 0.74 | 1.02 | 66% | <5.0 | 0.005 |
| 44 | 0.73 | 1.16 | 67% | <5.0 | 0.003 |

Figure 9:
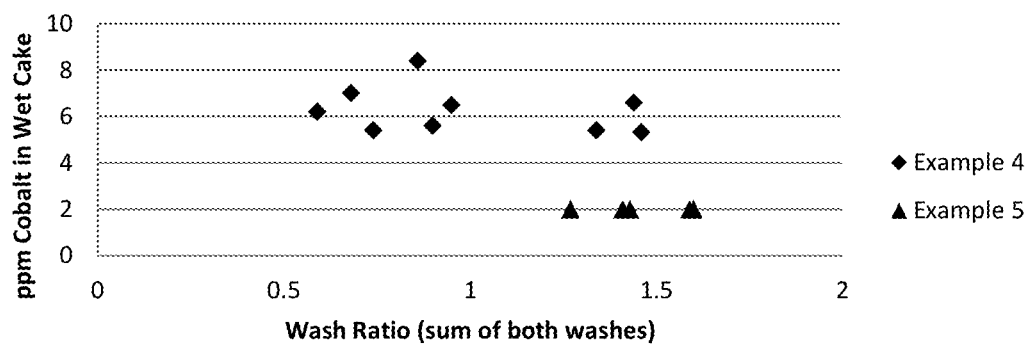
FIG. 9 is a graph illustrating the amount of cobalt remaining in a wet cake at a variety of wash ratios for a double wash event with a dewatering step preceding a final wash step.

FIG. 9 graphically illustrates that if a two wash step configuration is acceptable, the use of a water wash for the final wash step, as in Example 5, can reduce the amount of cobalt remaining in the cake as compared to no dewater step (Example 4) at equivalent wash ratios.

What is claimed is:

1. A process for treating a crude carboxylic acid (CCA) composition comprising:
   (a) feeding a CCA composition comprising a liquid and solids, said liquid comprising an organic solvent and said solids comprising dicarboxylic acid (DCA), to a filter cake formation zone to form:
      (i) a CCA wet cake composition comprising said DCA solids and a portion of said organic solvent, said CCA wet cake composition having a first liquid level; and
      (ii) a first mother liquor stream;
   (b) dewatering said CCA wet cake composition from step (a) in a dewatering zone to form:
      (i) a dewatered CCA wet cake composition having a second liquid level that is lower than the first liquid level or having no liquid level; and
      (ii) a second mother liquor stream; and
   (c) washing the dewatered CCA wet cake composition from step (b) with a wash stream in a wash zone to form:
      (i) a washed CCA wet cake composition; and
      (ii) a wash liquor stream.

2. The process of claim 1, wherein the organic solvent comprises acetic acid.

3. The process of claim 1, wherein the CCA composition contains 300 to 6,000 parts per million cobalt based on the weight of the CCA composition fed to the filter cake formation zone.

4. The process of claim 1, wherein the CCA composition fed to the filter cake formation zone has not been subjected to a step for hydrogenation prior to feeding the CCA composition to the filter cake formation zone.

5. The process of claim 1, wherein the first mother liquor stream comprises organic solvent in an amount of at least 95 wt. %, based on the weight of the mother liquor stream.

6. The process of claim 1, wherein the temperature of the first mother liquor stream is within a range of 50° C. to 100° C.

7. The process of claim 1, wherein the temperature and pressure within any one of the filter cake formation zone, the dewatering zone, and the wash zone, is within a range of 70° C. to 140° C., and within a range of 2 bar gauge to 5 bar gauge, respectively.

8. The process of claim 1, wherein the thickness of the CCA wet cake, the dewatered CCA wet cake, or the washed CCA wet cake is within a range of 2 to 5 inches.

9. The process of claim 1, wherein the duration of feeding the CCA wet cake composition to the filter cake formation zone is from 5 seconds to 30 seconds, the duration of dewatering the CCA wet cake composition in the dewatering zone is from 3 seconds to 30 seconds, and the duration of washing CCA wet cake composition in the washing zone is from 5 seconds to 30 seconds.

10. The process of claim 1, wherein an agent for dewatering in the dewatering zone comprises at least 80 volume % gas.

11. The process of claim 10, wherein a pressure drum filter is used and the flow rate standard is less than 0.14 standard L/sqcm/min at a pressure of 1-5 bar.

12. The process of claim 1, wherein the liquid volume of the second mother liquor stream is less than the liquid volume of the first mother liquor stream.

13. The process of claim 1, wherein the wash stream comprises at least 50 wt. % water based on the weight of the wash stream.

14. The process of claim 1, wherein the wash stream comprises at least 90 wt. % acetic acid based on the weight of the wash stream.

15. The process of claim 1, wherein the wash ratio of mass of wash to the mass of dry solids is at least 0.35:1 and up to 2:1.

16. The process of claim 1, wherein washed CCA wet cake composition is fed to a second dewatering zone after the wash zone to form a third mother liquor composition and a low moisture washed CCA wet cake composition.

17. The process of claim 1, wherein the washed CCA wet cake composition has a concentration of cobalt less than 50 ppm, based on the weight of the washed CCA wet cake composition, wherein said process utilizes one wash step and at a wash ratio of less than 1:1.

18. The process of claim 17, wherein the washed CCA wet cake composition has a concentration of cobalt less than 20 ppm, based on the weight of the washed CCA wet cake composition, wherein said process utilizes one wash step and at a wash ratio of less than 1:1.

19. The process of claim 17, wherein the washed CCA wet cake composition has a concentration of cobalt less than 15 ppm, based on the weight of the washed CCA wet cake composition, wherein said process utilizes one wash step and at a wash ratio of less than 1:1.

20. The process of claim 1, wherein one or more of the wash liquor streams are fed directly or indirectly to a waste water treatment facility without the use of a distillation column prior to introducing the wash liquor stream to quiescent basin in the waste water treatment facility.

21. The process of claim 1, further comprising a cake discharge zone.

22. The process of claim 21, wherein the washed CCA wet cake composition is discharged from the cake discharge zone by applying water to the CCA wet cake composition to erode the wet cake from the cake discharge zone and applying water to the filter media supporting the washed CCA wet cake composition.

23. The process of claim 22, wherein said water application is by a water spray.

24. The process of claim 23, wherein a back blow of gas is applied to the filter media during at least a portion of the water spray application.

25. The process of claim 1, wherein the CCA composition comprises at least 20 wt. % solids, and the solids comprise at least 80 wt. % isophthalic acid.

26. The process of claim 2, wherein the CCA composition comprises at least 20 wt. % solids, and the solids comprise at least 80 wt. % isophthalic acid.

27. The process of claim 3, wherein the CCA composition comprises at least 20 wt. % solids, and the solids comprise at least 80 wt. % isophthalic acid.

28. The process of claim 4, wherein the CCA composition comprises at least 20 wt. % solids, and the solids comprise at least 80 wt. % isophthalic acid.

29. The process of claim 5, wherein the CCA composition comprises at least 20 wt. % solids, and the solids comprise at least 80 wt. % isophthalic acid.

30. The process of claim 6, wherein the CCA composition comprises at least 20 wt. % solids, and the solids comprise at least 80 wt. % isophthalic acid.

31. The process of claim 7, wherein the CCA composition comprises at least 20 wt. % solids, and the solids comprise at least 80 wt. % isophthalic acid.

32. The process of claim 8, wherein the CCA composition comprises at least 20 wt. % solids, and the solids comprise at least 80 wt. % isophthalic acid.

33. The process of claim 9, wherein the CCA composition comprises at least 20 wt. % solids, and the solids comprise at least 80 wt. % isophthalic acid.

34. The process of claim 10, wherein the CCA composition comprises at least 20 wt. % solids, and the solids comprise at least 80 wt. % isophthalic acid.

35. The process of claim 11, wherein the CCA composition comprises at least 20 wt. % solids, and the solids comprise at least 80 wt. % isophthalic acid.

36. The process of claim 12, wherein the CCA composition comprises at least 20 wt. % solids, and the solids comprise at least 80 wt. % isophthalic acid.

37. The process of claim 13, wherein the CCA composition comprises at least 20 wt. % solids, and the solids comprise at least 80 wt. % isophthalic acid.

38. The process of claim 14, wherein the CCA composition comprises at least 20 wt. % solids, and the solids comprise at least 80 wt. % isophthalic acid.

39. The process of claim 15, wherein the CCA composition comprises at least 20 wt. % solids, and the solids comprise at least 80 wt. % isophthalic acid.

40. The process of claim 16, wherein the CCA composition comprises at least 20 wt. % solids, and the solids comprise at least 80 wt. % isophthalic acid.

41. The process of claim 17, wherein the CCA composition comprises at least 20 wt. % solids, and the solids comprise at least 80 wt. % isophthalic acid.

42. The process of claim 18, wherein the CCA composition comprises at least 20 wt. % solids, and the solids comprise at least 80 wt. % isophthalic acid.

43. The process of claim 19, wherein the CCA composition comprises at least 20 wt. % solids, and the solids comprise at least 80 wt. % isophthalic acid.

44. The process of claim 20, wherein the CCA composition comprises at least 20 wt. % solids, and the solids comprise at least 80 wt. % isophthalic acid.

45. The process of claim 1, wherein the CCA composition comprises at least 20 wt. % solids, and the solids comprise at least 80 wt. % terephthalic acid.

46. The process of claim 2, wherein the CCA composition comprises at least 20 wt. % solids, and the solids comprise at least 80 wt. % terephthalic acid.

47. The process of claim 3, wherein the CCA composition comprises at least 20 wt. % solids, and the solids comprise at least 80 wt. % terephthalic acid.

48. The process of claim 4, wherein the CCA composition comprises at least 20 wt. % solids, and the solids comprise at least 80 wt. % terephthalic acid.

49. The process of claim 5, wherein the CCA composition comprises at least 20 wt. % solids, and the solids comprise at least 80 wt. % terephthalic acid.

50. The process of claim 6, wherein the CCA composition comprises at least 20 wt. % solids, and the solids comprise at least 80 wt. % terephthalic acid.

51. The process of claim 7, wherein the CCA composition comprises at least 20 wt. % solids, and the solids comprise at least 80 wt. % terephthalic acid.

52. The process of claim 8, wherein the CCA composition comprises at least 20 wt. % solids, and the solids comprise at least 80 wt. % terephthalic acid.

53. The process of claim 9, wherein the CCA composition comprises at least 20 wt. % solids, and the solids comprise at least 80 wt. % terephthalic acid.

54. The process of claim 10, wherein the CCA composition comprises at least 20 wt. % solids, and the solids comprise at least 80 wt. % terephthalic acid.

55. The process of claim 11, wherein the CCA composition comprises at least 20 wt. % solids, and the solids comprise at least 80 wt. % terephthalic acid.

56. The process of claim 12, wherein the CCA composition comprises at least 20 wt. % solids, and the solids comprise at least 80 wt. % terephthalic acid.

57. The process of claim 13, wherein the CCA composition comprises at least 20 wt. % solids, and the solids comprise at least 80 wt. % terephthalic acid.

58. The process of claim 14, wherein the CCA composition comprises at least 20 wt. % solids, and the solids comprise at least 80 wt. % terephthalic acid.

59. The process of claim 15, wherein the CCA composition comprises at least 20 wt. % solids, and the solids comprise at least 80 wt. % terephthalic acid.

60. The process of claim 16, wherein the CCA composition comprises at least 20 wt. % solids, and the solids comprise at least 80 wt. % terephthalic acid.

61. The process of claim 17, wherein the CCA composition comprises at least 20 wt. % solids, and the solids comprise at least 80 wt. % terephthalic acid.

62. The process of claim 18, wherein the CCA composition comprises at least 20 wt. % solids, and the solids comprise at least 80 wt. % terephthalic acid.

63. The process of claim 19, wherein the CCA composition comprises at least 20 wt. % solids, and the solids comprise at least 80 wt. % terephthalic acid.

64. The process of claim 20, wherein the CCA composition comprises at least 20 wt. % solids, and the solids comprise at least 80 wt. % terephthalic acid.

65. A process for treating a crude carboxylic acid (CCA) composition comprising:
   (a) feeding a CCA composition comprising a liquid and solids, said liquid comprising an organic solvent and said solids comprising dicarboxylic acid (DCA), to a filter cake formation zone to form:
      (i) a CCA wet cake composition comprising said DCA solids and a portion of said organic solvent, said CCA wet cake composition having a first liquid level; and
      (ii) a first mother liquor stream;
   (b) washing said CCA wet cake composition from step (a) with an intermediate wash stream to form:
      (i) an intermediate washed CCA wet cake composition having a second liquid level that is lower than the first liquid level or having no liquid level; and
      (ii) an intermediate wash liquor stream; and
   (c) dewatering said intermediate washed CCA wet cake composition from step (b) to form:
      (i) a dewatered CCA wet cake composition having a second liquid level that is lower than the first liquid level or having no liquid level; and
      (ii) a second mother liquor stream; and
   (d) washing the dewatered CCA wet cake composition from step (c) with a second wash stream in a wash zone to form:
      (i) a washed CCA wet cake composition; and
      (ii) a wash liquor stream.

66. The process of claim 65, wherein the washed CCA wet cake composition is fed to a second dewatering zone after the wash zone (d) to form a third mother liquor composition and a low moisture washed CCA wet cake composition.

67. The process of claim 66, wherein the low moisture CCA wet cake composition has a moisture content of 20 wt. % or less without a drying step, based on the weight of the low moisture washed CCA wet cake composition.

68. The process of claim 65, wherein the washed CCA composition has a concentration of cobalt less than 20 ppm, based on the weight of the washed CCA wet cake composition, wherein said process utilizes a wash ratio at each wash step of less than 1:1.

69. The process of claim 65, wherein the washed CCA wet cake composition has a concentration of cobalt less than 10 ppm, based on the weight of the washed CCA wet cake composition, wherein said process utilizes a wash ratio of less than 1:1 at each wash step.

70. The process of claim 65, wherein the thickness of the washed CCA wet cake is within a range of 3 to 5 inches.

71. The process of claim 65, wherein the agent for dewatering comprising at least 80 volume % gas.

72. The process of claim 71, wherein the gas comprises at least 80% nitrogen.

73. The process of claim 65, wherein the process steps (a)-(d) are conducted in a pressure drum filter.

74. The process of claim 65, wherein the washed CCA wet cake composition comprises at least 5 wt. % moisture and no more than 100 ppm of the organic solvent.

75. The process of claim 74, wherein the washed CCA wet cake composition comprises at least 30 wt. % moisture and no more than 5 ppm of the organic solvent.

* * * * *